United States Patent
Ambrosina et al.

(10) Patent No.: US 9,581,251 B2
(45) Date of Patent: Feb. 28, 2017

(54) FLUID FLOW REGULATOR ASSEMBLY

(71) Applicant: Ivenix, Inc., Amesbury, MA (US)

(72) Inventors: Jesse E. Ambrosina, Topsfield, MA (US); Benjamin G. Powers, Portsmouth, NH (US); Alexander J. Segit, Eliot, ME (US)

(73) Assignee: Ivenix, Inc., Amesbury, MA (US)

( * ) Notice: Subject to any disclaimer, the term of this patent is extended or adjusted under 35 U.S.C. 154(b) by 77 days.

(21) Appl. No.: 14/540,081

(22) Filed: Nov. 13, 2014

(65) Prior Publication Data

US 2015/0137017 A1    May 21, 2015

Related U.S. Application Data

(60) Provisional application No. 61/904,809, filed on Nov. 15, 2013.

(51) Int. Cl.
| | |
|---|---|
| *F16K 3/02* | (2006.01) |
| *B23P 15/00* | (2006.01) |
| *A61M 5/168* | (2006.01) |
| *A61M 5/14* | (2006.01) |
| *A61M 5/36* | (2006.01) |

(52) U.S. Cl.
CPC ....... *F16K 3/0209* (2013.01); *A61M 5/16804* (2013.01); *A61M 5/16877* (2013.01); *B23P 15/001* (2013.01); *A61M 5/1408* (2013.01); *A61M 5/16827* (2013.01); *A61M 5/16854* (2013.01); *A61M 5/16881* (2013.01); *A61M 5/36* (2013.01); *A61M 2005/16863* (2013.01); *A61M 2205/3334* (2013.01); *A61M 2205/3337* (2013.01); *Y10T 29/49412* (2015.01)

(58) Field of Classification Search
CPC ..... F16K 5/12; F16K 3/34; F16K 1/54; F16K 1/34
USPC .......................... 251/205, 208, 209
See application file for complete search history.

(56) References Cited

U.S. PATENT DOCUMENTS

| | | | |
|---|---|---|---|
| 2,911,008 A | * | 11/1959 | Du Bois ........... A61M 5/16881 137/625.18 |
| 3,620,500 A | | 11/1971 | Santomieri |
| 3,685,787 A | | 8/1972 | Adelberg |
| 3,785,378 A | | 1/1974 | Stewart |
| 3,877,428 A | | 4/1975 | Seagle et al. |
| 3,900,184 A | | 8/1975 | Burke et al. |
| 4,065,093 A | | 12/1977 | Phillips |

(Continued)

FOREIGN PATENT DOCUMENTS

| | | |
|---|---|---|
| WO | WO 86/04821 A1 | 8/1986 |
| WO | WO 01/33118 A1 | 5/2001 |
| WO | 2006/009369 A1 | 1/2006 |

OTHER PUBLICATIONS

International Search Report, PCT/US2014/065341, Feb. 26, 2015, pp. 4.

(Continued)

*Primary Examiner* — Matthew W Jellett
(74) *Attorney, Agent, or Firm* — Chapin IP Law, LLC

(57) ABSTRACT

A fluid flow resistance assembly includes a fluid pathway. A width of the fluid pathway orthogonal to a flow of fluid through the fluid pathway varies along its length. Positioning of one or more ports at different locations over the fluid pathway at different locations controls a flow rate of fluid.

39 Claims, 18 Drawing Sheets

(56) References Cited

U.S. PATENT DOCUMENTS

| | | | | |
|---|---|---|---|---|
| 4,380,250 | A * | 4/1983 | Stoll | F16K 3/34 137/556 |
| 4,406,440 | A | 9/1983 | Kulle et al. | |
| 4,685,654 | A | 8/1987 | Hu | |
| 4,776,838 | A | 10/1988 | Sainte-Rose et al. | |
| 4,802,506 | A * | 2/1989 | Aslanian | A61M 5/16881 137/556 |
| 5,005,604 | A * | 4/1991 | Aslanian | A61M 5/16881 137/556 |
| 5,356,376 | A | 10/1994 | Milijasevic et al. | |
| 5,524,863 | A * | 6/1996 | Davis | B08B 9/00 137/625.32 |
| 5,803,917 | A * | 9/1998 | Butterfield | A61M 5/16859 604/67 |
| 6,230,607 | B1 * | 5/2001 | Rehrl | A61C 1/0038 251/208 |
| 6,726,175 | B1 | 4/2004 | Saba et al. | |
| 6,808,162 | B2 * | 10/2004 | Tranovich | F16K 5/12 251/121 |
| 6,916,010 | B2 | 7/2005 | Beck et al. | |
| 7,028,927 | B2 | 4/2006 | Mermet | |
| 7,111,643 | B2 * | 9/2006 | Oh | F16K 5/0605 137/625.41 |
| 7,668,731 | B2 * | 2/2010 | Martucci | A61M 5/142 600/300 |
| 8,029,480 | B2 * | 10/2011 | Lee | A61M 5/141 251/149.5 |
| 8,313,308 | B2 * | 11/2012 | Lawless | A61M 5/14224 417/44.1 |
| 2004/0140444 | A1 | 7/2004 | Beck | |
| 2007/0083176 | A1 | 4/2007 | Voege et al. | |
| 2012/0053556 | A1 | 3/2012 | Lee | |

OTHER PUBLICATIONS

Supplementary European Search Report, EP 14 86 2388, Oct. 5, 2016, pp. 7.

\* cited by examiner

FLUID FLOW REGULATOR ASSEMBLY

RELATED APPLICATIONS

This application claims the benefit of U.S. Provisional Patent Application Ser. No. 61/904,809 entitled "FLOW REGULATION DEVICE FOR ADMINISTRATION OF INTRAVENOUS FLUIDS,"filed on Nov. 15, 2013, the entire teachings of which are incorporated herein by this reference.

BACKGROUND

Conventional flow regulation devices have been developed to restrict a flow of fluid. One common example is set forth in issued U.S. Pat. No. 3,900,184, entitled, "Roller Clamp for Tubing." This type of device relies on use of common infusion tubing to deliver fluid. In general, as a roller is moved from one end of a housing to the other, a tube within the housing is compressed to restrict the flow of fluid to a target recipient.

One type of deficiency associated with the roller clamp technology is that it is only able to make very coarse flow adjustments based on movement of the roller clamp. Another deficiency associated with roller clamp technology is that the flow rate setting is prone to drifting. This is due to the elasticity of tubing relaxing over time, resulting in an increase in a size of a passageway and respective flow rate of delivering fluid. This creates potentially dangerous situation if undetected.

As a result of the need for higher precision in-line fluid flow control, more precise flow control technology has been developed. For example, both issued U.S. Pat. No. 6,916,010 and issued U.S. Pat. No. 3,877,428 describe devices for controlling a flow rate of fluid. These devices provide substantial improvements over conventional pinch valves with roller clamps. However, they do not provide accurate and repeatable flow needed for modern infusion applications.

BRIEF DESCRIPTION OF EMBODIMENTS

Embodiments herein include unique ways of controlling a flow of fluid to a target recipient. For example, in one embodiment, the fluid flow control apparatus includes a length of fluid pathway, a first port, and a second port. The length of fluid pathway can be straight, curved, winding, etc. To set a flow rate, an opening of the first port is positioned over the fluid pathway at a first location along its length. An opening of the second port is positioned over the fluid pathway at a second location along its length.

In one embodiment, the fluid pathway is movable with respect to the opening of the first port and the opening of the second port to adjust a fluid flow resistance through a combination of the first port, a portion of the fluid pathway between the first location and the second location, and the second port. Alternatively, one or more of the openings associated with the first port and the second port can be movable with respect to the fluid pathway.

In accordance with further embodiments, the opening of the first port is disposed to be at a fixed offset distance with respect to the opening of the second port.

Attributes of the fluid pathway at the first location and the second location as well as attributes of a respective fluid-tight pathway between the first location and the second location control an amount of fluid resistance provided by the fluid pathway between the first location and the second location. More specifically, an aperture (such as a width or orifice) of the fluid pathway into the opening of the first port at the first location and an aperture (such as a width or orifice) of the fluid pathway into the opening of the second port at the second location substantially affects a fluid flow resistance setting of the fluid flow control apparatus. In one embodiment, a width and/or depth of the fluid pathway at the first location into the opening of the first port is substantially different than a width and/or depth of the fluid pathway at the second location into the opening of the second port.

In one embodiment, the width of the fluid pathway orthogonal to a flow of fluid through the fluid pathway varies linearly or nonlinearly along the length of the fluid pathway. For example, the width of the fluid pathway orthogonal to a flow of fluid through the fluid pathway can be configured to taper along the length of the fluid pathway; conversely, certain portions along the length of the fluid pathway can be a constant width. As mentioned, fluid resistance provided by the fluid flow control apparatus can depend at least in part on the width of the fluid pathway at the first location and width of the fluid pathway at the second location over which the respective first port and the second port are positioned.

As mentioned, a cross-sectional flow area (such as based on depth and width) of the fluid pathway orthogonal to a flow of fluid through the fluid pathway can vary along the length. In other words, in addition to tapering of a width of the channel along the length of the pathway, a diameter and/or depth of the channel orthogonal to a flow of respective fluid also can taper or vary along the fluid pathway. Larger cross-sectional flow areas (such as orthogonal to flow cross-sectional areas of larger diameter) of the fluid pathway provide lower resistance to passage of fluid; conversely, smaller cross-sectional flow areas (such as orthogonal to flow cross-sectional areas of smaller diameter) of the fluid pathway provide higher resistance to passage of fluid between the first port and the second port. Again, widths of the respective fluid pathway at respective locations of the first port and second port also may dictate fluid flow as well.

In accordance with further embodiments, the fluid pathway (such as a grooved channel of varying width and diameter disposed in an assembly element) is selectively movable with respect to the opening of the first port and/or the opening of the second port to adjust a fluid flow resistance through a combination of the first port, a portion of the fluid pathway between the first location and the second location, and the second port. If desired, the opening of the first port can be disposed on an assembly element at a fixed offset with respect to the opening of the second port.

In accordance with another embodiment, a position of the opening of the first port is selectively adjustable with respect to the fluid pathway to adjust a fluid flow resistance provided by a combination of the first port, a portion of the fluid pathway between the first location and the second location, and the second port. In one embodiment, the fluid pathway is disposed as a hollowed volume on a substantially planar facing of a first assembly element of the flow control apparatus. As mentioned, a width of the hollowed volume and/or depth on the planar facing varies along the length In contrast to conventional technology, embodiments herein address flow accuracy and flow control resolution by means of a contoured flow channel. In a further example embodiment, the contoured flow channel can be configured to create a linearly proportional flow rate per degree of rotation. That is, a relationship between a change in angular rotation of the second flow control assembly element (including the fluid pathway) with respect to the first flow control assembly element (including the first port and the second port) and resulting change in the flow rate of fluid through the fluid pathway is linear. When driven by an automatic control system such as a fluid resistant drive in a fluid delivery system, linear control capability (such as a linearized flow rate versus angular position of the rotatable flow control assembly) afforded by the flow control apparatus enables precise flow regulation via a closed loop control algorithm.

These and other more specific embodiments are disclosed in more detail below.

As discussed herein, further note that techniques herein are well suited for accurately controlling a flow resistance and/or a flow of fluid to a recipient (any suitable type of entity). However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where suitable, that each of the concepts can optionally be executed independently of each other or in combination with each other. Accordingly, the one or more present inventions as described herein can be embodied and viewed in many different ways.

Also, note that this preliminary discussion of embodiments herein purposefully does not specify every embodiment and/or incrementally novel aspect of the present disclosure or claimed invention(s). Instead, this brief description only presents general embodiments and corresponding points of novelty over conventional techniques. For additional details and/or possible perspectives (permutations) of the invention(s), the reader is directed to the Detailed Description section and corresponding figures of the present disclosure as further discussed below.

Figure 1:
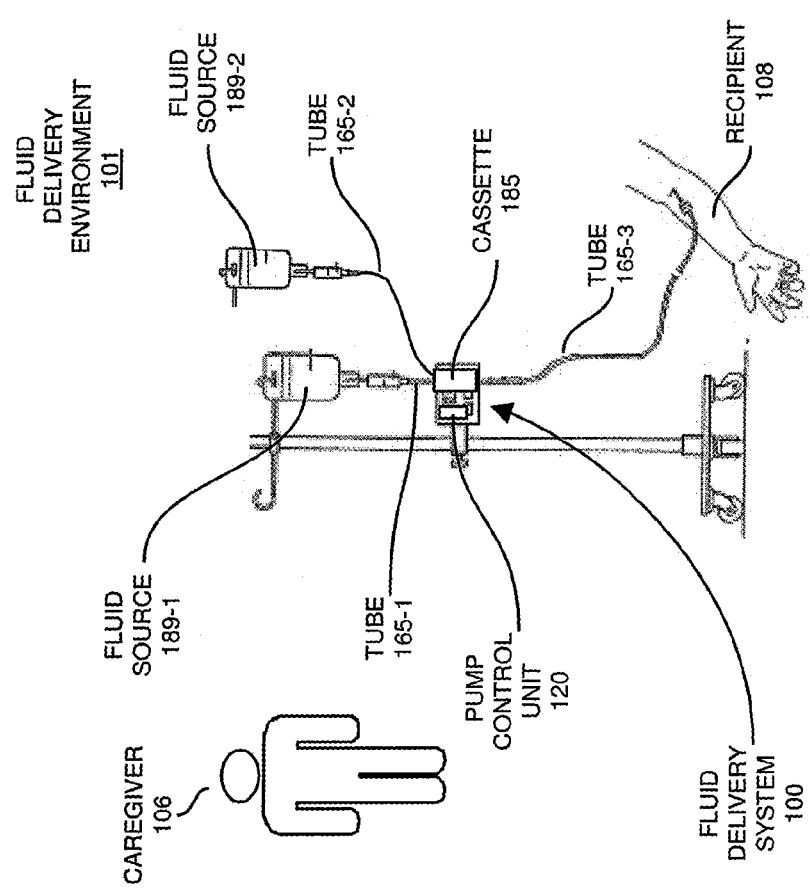
FIG. 1 is an example diagram of a fluid delivery environment according to embodiments herein.

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION AND FURTHER SUMMARY OF EMBODIMENTS

More specifically, FIG. 1 is an example diagram illustrating a fluid delivery environment and fluid delivery system according to embodiments herein.

As shown, the fluid delivery system 100 disposed in fluid delivery environment 101 includes a fluid source 189-1 (first fluid source), second fluid source 189-2 (second fluid source), pump control unit 120, and disposable tube assembly (such as a combination of cassette 185, tube 165-1, tube 165-2, and tube 165-3).

In this example embodiment, cassette 185 is already inserted in a corresponding cavity of pump control unit 120. Caregiver 106 programs the fluid delivery system 100 to deliver fluid at a desired rate to recipient 108.

In general, based on a desired flow rate set by caregiver 106, during operation, pump control unit 120 controls a corresponding pump resource (such as one or more diaphragm pumps), valves, etc., in cassette 185 to deliver fluid from fluid sources 189 through tube 165-1, cassette 185, and tube 165-3 to recipient 108 (any suitable type of entity such as a human, a pet, a container, etc.).

Figure 2:
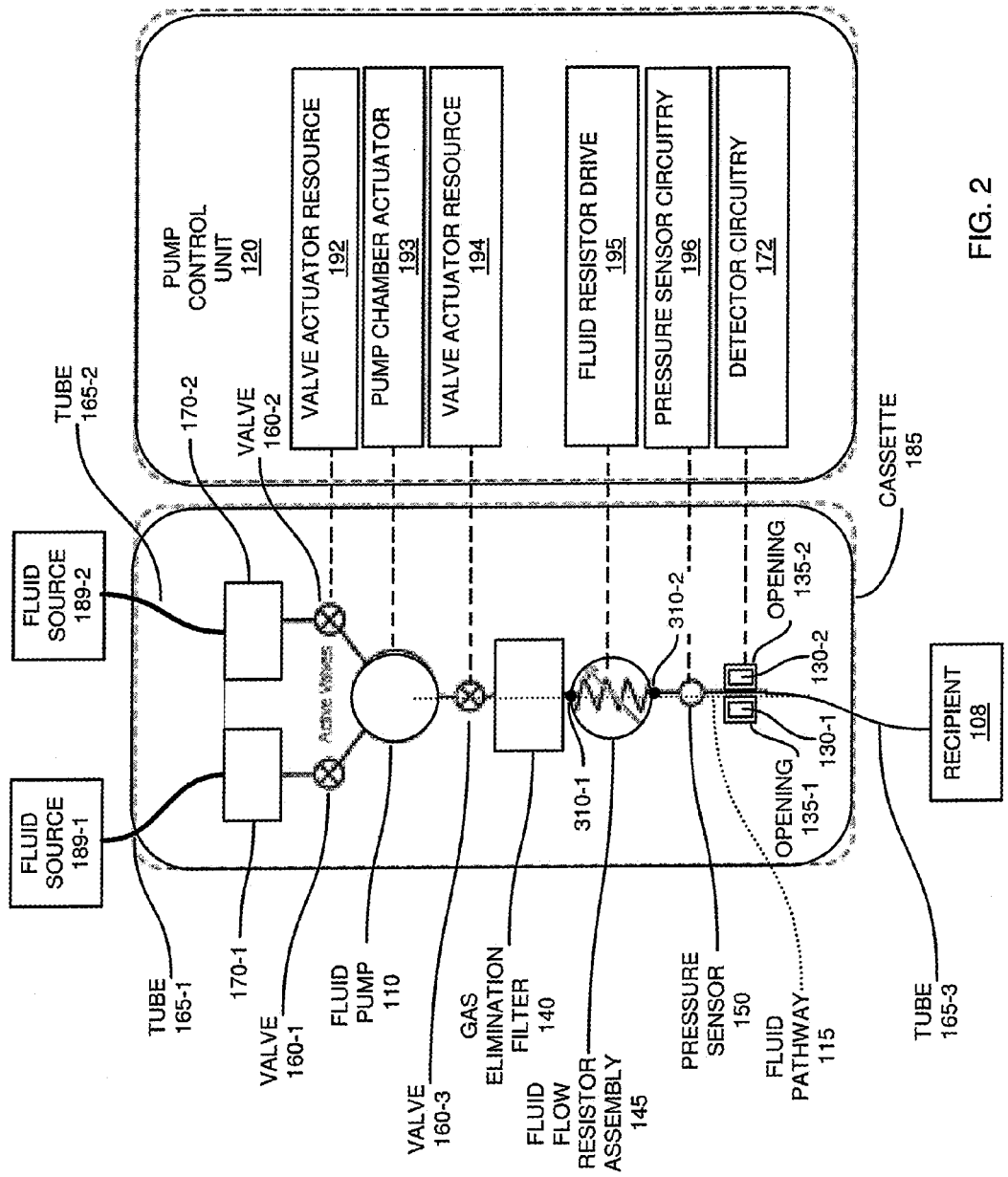
FIG. 2 is an example diagram illustrating attributes of a fluid flow resistor assembly disposed in a cassette assembly according to embodiments herein.

FIG. 2 is an example diagram illustrating a disposable cassette and corresponding pump control unit according to embodiments herein.

As previously discussed, embodiments herein include cassette 185 that fits into a corresponding cavity 204 of fluid delivery system 100.

In one embodiment, in addition to including tube 165-1 and tube 165-2, note that a disposable assembly can further include tube 165-3. As mentioned, a combination of resources including tube 165-1, tube 165-2, tube 165-3, and cassette 185 represent an assembly such as a disposable tube set. As its name suggests, the disposable tube set can be thrown away after it is used to deliver a corresponding fluid to an entity such as recipient 108 (such as a patient).

The pump controller unit 120 can be used in conjunction with each new disposable tube set to deliver fluid to a next patient. Thus, the pump controller unit 120 is reusable across multiple patients. However, as mentioned, each respective disposable tube set is typically used to deliver fluid to only one patient.

As shown and as previously discussed, insertion of cassette 185 into the corresponding cavity 204 of the fluid delivery system 100 provides coupling between resources in the cassette 185 and control resources in pump control unit 120.

For example, when the cassette 185 is inserted into cavity 204 of the fluid delivery system 100, valve actuator resource 192 (e.g., valve controllers) become coupled to corresponding valves 160 (valve 160-1 and valve 160-2) in the cassette 185. During pump operation, valve actuator resource 192 in the pump control unit 120 controls settings of valves 160-1 and 160-2 to respective open and close states. Further in this example embodiment, note that valve actuator resource 194 in the pump controller unit 120 controls valve 160-3 to control a flow of fluid along fluid pathway 115 to recipient 182.

The valve actuator resources in the pump controller unit 120 can control the respective valves 160 in any suitable manner depending on the type of the valves. For example, depending on the type of valves, via control input from the valve actuator resources in the pump control unit 120, the valves 160 can be electromechanically controlled, hydraulically controlled, pneumatically controlled, etc.

When pumping respective fluid from one or more fluid sources 189, the pump control unit 120 controls valves 160 to respective open and closed states as desired.

For example, to draw fluid from the first fluid source 189-1 through the primary inlet 170-1 into a respective pump chamber of fluid pump 110, the pump control unit 120 opens valve 160-1 and closes valve 160-2 and valve 160-3. While only valve 160-1 is open, the pump control unit 120 controls pump chamber actuator 193 to draw fluid through tube 165-1 into the pump chamber of fluid pump 110.

After drawing sufficient amount of fluid into the pump chamber of fluid pump 110, the pump control unit 120 closes valves 160-1 and valve 160-2 and opens valve 160-3. While only valve 160-3 is open, the pump control unit 120 controls pump chamber actuator 193 to force the fluid in the pump chamber fluid pump 110 downstream along fluid pathway 115. Note further that embodiments herein can include switching between drawing fluids from the different fluid sources 189 and delivering such fluids to the recipient 108. For example, in a first pump cycle, the pump controller unit 120 can be configured to control valves 160 (valve 160-1, valve 160-2, valve 160-3) to deliver fluid from fluid source 189-1 to recipient 108 in a manner as previously discussed; in a second pump cycle, the pump controller unit 120 can be configured to control valves 160 to deliver fluid from fluid source 189-2 to recipient 108 in a manner as previously discussed; in a third pump cycle, the pump controller unit 120 can be configured to control valves 160 to deliver fluid from fluid source 189-1 to recipient 108 in a manner as previously discussed; in a fourth pump cycle, the pump controller unit 120 can be configured to control valves 160 to deliver fluid from fluid source 189-2 to recipient 108 in a manner as previously discussed; and so on. Accordingly, a single fluid pump 110 (such as diaphragm pump) in cassette 185 can be used to switch between delivering fluid from different sources 189 to a recipient 108.

As further shown, note that cassette 185 can further include gas elimination filter 140 disposed downstream with respect to valve 160-3 in fluid pathway 115.

In one embodiment, as shown, the gas elimination filter 140 is disposed upstream with respect to fluid flow resistor assembly 145. Disposing the gas elimination filter 140 upstream with respect to the fluid flow resistor assembly 145 ensures that the gas elimination filter 140 remains under positive pressure (e.g., a higher pressure than a pressure at a location monitored by pressure sensor 150 as discussed below) during fluid delivery.

As its name suggests, and as previously discussed, the gas elimination filter 140 disposed in cassette 185 removes any air or gases from the fluid traveling downstream along fluid pathway 115 towards fluid flow resistor assembly 145. In one embodiment, the gas elimination filter 140 vents any detected gas out of the fluid pathway 115 into open atmosphere.

Fluid resistor drive 195 controls a degree to which the fluid flow resistor assembly 145 resists a corresponding flow of the fluid along fluid pathway 115 towards recipient 108. Increased resistance provided by the fluid flow resistor assembly 145 reduces a flow rate of fluid long pathway 115 to recipient 108. Decreased resistance provided by the fluid flow resistor assembly 145 increases a flow rate of fluid long pathway 115 to recipient 108.

Port 310-1 receives fluid passing along fluid pathway 115 through gas elimination filter 140. Port 310-2 outputs respective fluid in fluid pathway 115 downstream towards pressure sensor 150.

In a similar manner as previously discussed, the fluid flow resistor assembly 145 can be controlled in any suitable manner. For example, the fluid flow resistor assembly 145 can be electromechanically controlled, hydraulically controlled, pneumatically controlled, etc., via fluid resistor drive 195.

In accordance with yet further embodiments, cassette 185 further includes pressure sensor 150 disposed in fluid pathway 115 downstream with respect to fluid flow resistor assembly 145.

In one non-limiting example embodiment, the pressure sensor 150 monitors a pressure of fluid disposed and passing through a corresponding location along fluid pathway 115 as shown. Via pressure sensor circuitry 196 in communication with pressure sensor 150, a flow control monitoring algorithm executed by the pump control unit 120 is able to determine a pressure of fluid delivered to the recipient 108 at a downstream location in fluid pathway 115 with respect to the fluid flow resistor assembly 145.

In one embodiment, the pressure sensor circuitry 196 detects when there is a blockage downstream preventing delivery of corresponding fluid to a recipient 108. For example, in one embodiment, when the pressure sensor circuitry 196 detects that the pressure at the location monitored by pressure sensor 150 is above a threshold value, the pressure sensor circuitry 196 generates a corresponding signal indicating a blockage condition and/or inability to deliver fluid to the recipient 108. Detecting pressure below the threshold value generally indicates that there is no blockage downstream and that the fluid is being delivered to the recipient 108, which is desired.

During pumping of fluid to recipient 108 via control of the fluid pump 110 as previously discussed, gas elimination filter 140 typically removes gas from the infusion line (fluid pathway 115) before it reaches the detector elements 130.

If the gas elimination filter 140 fails for some reason, and bubbles are detected by one or more detector elements 130-1 and 130-2, the bubble detector circuitry 172 generates a corresponding signal to pump control unit 120 to close the fluid flow resistor assembly 145 to stop flow. The corresponding signal indicates to the pump control unit 120 to discontinue delivery of corresponding fluid to the recipient 108. This prevents any gas in the fluid in fluid pathway 115 from being delivered to recipient 108 in the event that the gas elimination filter 140 happens to fail to remove gas.

By further way of non-limiting example, in one embodiment, in response to receiving an indication that bubbles are detected in fluid being delivered to the corresponding recipient 108, the pump control unit 120 can be configured to close one or more valves such as valve 160-1, valve 160-2, valve 160-3 and/or deactivate fluid pump 110 to discontinue delivery of fluid to the recipient 108.

Thus, embodiments herein can include a disposable cassette 185 including fluid pathway 115. The fluid pathway 115 includes gas elimination filter 140 and a flow resistor 145. The gas elimination filter 140 is disposed in the fluid pathway 115 downstream of the fluid pump 110. The flow resistor 145 is disposed in the fluid pathway 115 downstream from the gas elimination filter 140. As previously discussed, further embodiments of the cassette 185 can include a pressure sensor 150 as shown. Pressure sensor 150 monitors a pressure of fluid in the fluid pathway 115 at a location in the fluid pathway between the flow resistor 145 and the location of the fluid pathway 115 between the first detector element 130-1 and second detector element 130-2.

Figure 3:
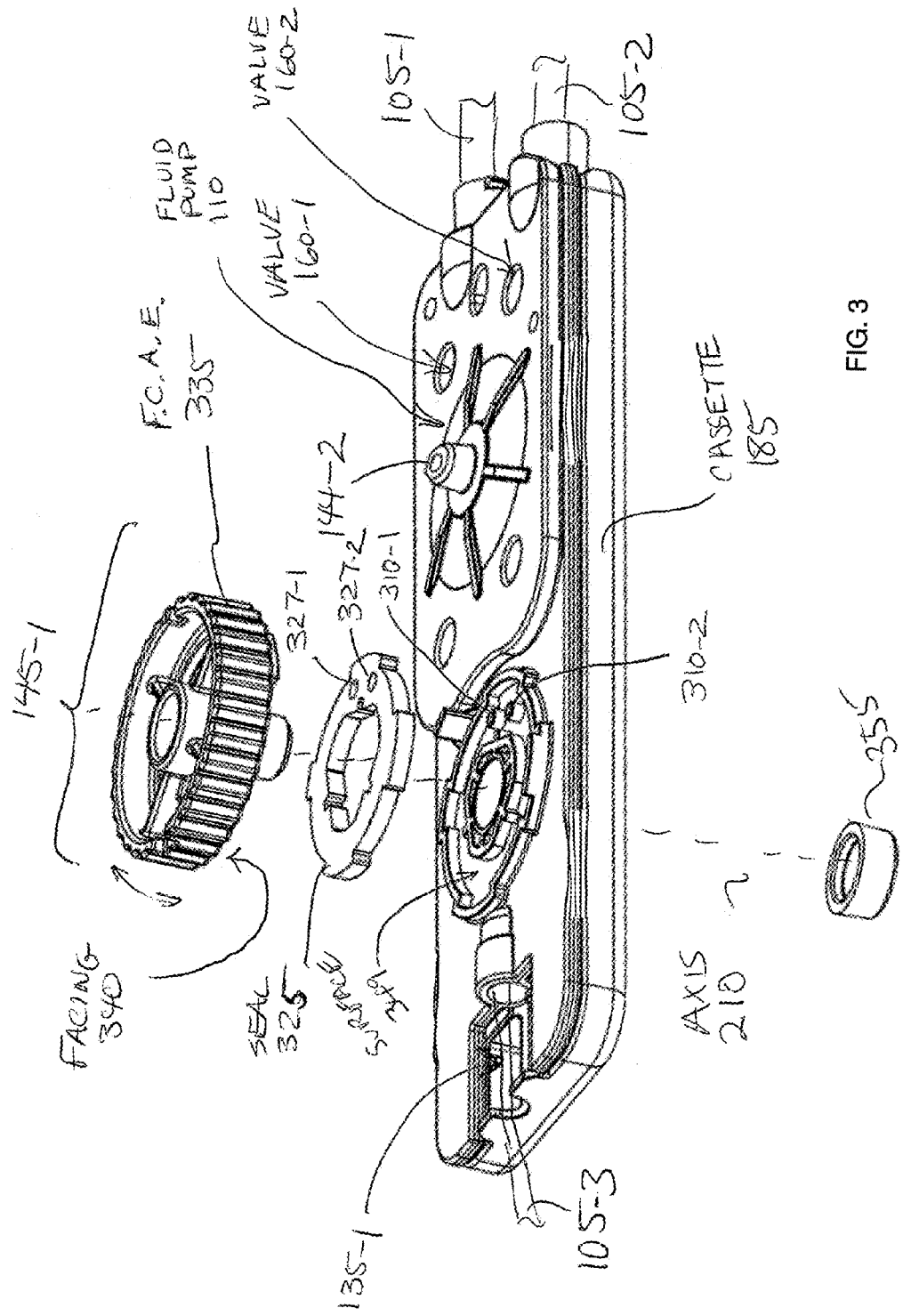
FIG. 3 is an example perspective view diagram illustrating a cassette assembly and corresponding exploded view of a fluid flow resistor assembly according to embodiments herein.

FIG. 3 is an example perspective view diagram illustrating a cassette assembly and corresponding exploded view of a fluid flow resistor assembly according to embodiments herein.

In this example embodiment, the fluid flow resistor assembly 145-1 includes a first flow control assembly element 335, a second flow control assembly element (such as seal 325), port 310-1, port 310-2, and fastener 355. In one embodiment, the seal 325 is an elastomeric seal (a.k.a., rubber).

The seal 325 includes ports 327-1 and 327-2.

Note that port 310-1, port 310-2, port 327-1, and port 3 27-2 can be located at any suitable location with respect to flow control assembly element 335 and axis 210.

The first flow control assembly element 335 and ports 310 disposed in cassette 185 can be made of rigid plastic or other suitable material. As shown, the ports 310 protrude from the respective surface of cassette 185. Alternatively, the ports 310 can be flush with respect to a surface of the cassette 185.

After installation, fastener 355 (such as formed via gluing, welding, snap-fit, etc.) secures flow control assembly element 335 to the cassette 185, compressing facing 340 to a respective surface of seal 325. The opposite facing of seal 325 is compressed and in contact with the surface 349 of the cassette 185.

Port 327-1 provides a fluid-tight pathway between port 310-1 of cassette 185 and a first location on a respective surface of facing 340. Port 327-2 provides a fluid-tight pathway between port 310-2 and a second location on the respective surface of facing 340.

Further, as previously discussed, cassette 185 includes fluid pump 110 (any suitable type of pump such as a diaphragm pump assembly). The pump control unit 120 controls settings of the respective valves 160 as well as a flow of gas (such as a negative pressure) to port 144-2 of the fluid pump 110 to draw fluid from one or more respective fluid sources 189 into a respective chamber fluid pump 110. Subsequent application of positive pressure to the port pushes fluid in the chamber of the fluid pump 110 downstream along fluid pathway 115.

Yet further, as previously discussed, fluid pathway 115 includes fluid flow resistor assembly 145-1 controlled by fluid resistor drive 195. In one embodiment, the fluid resistant drive 195 controls an angular or rotational orientation 375 of the flow control assembly element 335 with respect to axis 210 to control a respective flow of fluid further down fluid pathway 115 through tube 105-3 to recipient 108.

In one embodiment, as will be further discussed below, the port 310-1 receives fluid passing along fluid pathway 115 from gas elimination filter 140. Fluid received from port 310-1 and port 327-1 passes through a channel disposed between facing 340 of the flow control assembly element 335 and opposing facing of seal 325 to port 327-2 and port 310-2. Port 310-2 further conveys the fluid along the fluid pathway 115 of cassette 185 towards pressure sensor 150 as previously discussed.

Note that, depending on the embodiment, the radial distance between axis 210 and a location of port 310-1 and port 327-1 and a location of port 310-2 and port 327-2 can be the same or different value as further discussed below.

In accordance with further embodiments, the flow control assembly element 335 is rotatable with respect to axis 210. The fluid resistor drive 195 controls an orientation of the flow control assembly element 335 (adjusting a positioning of the tapered channel with respect to the ports 310 and/or ports 327) to control a flow of fluid from the fluid source to the target recipient 108.

Figure 4:
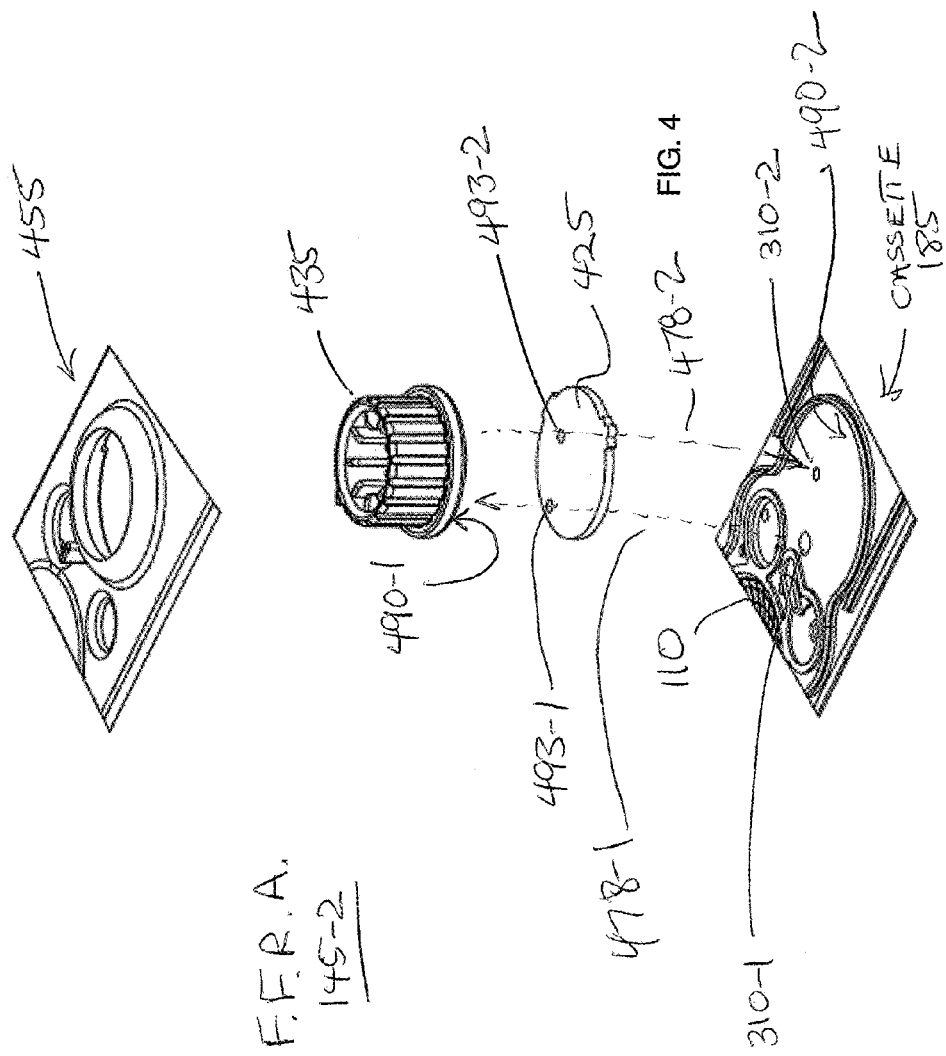
FIG. 4 is an example perspective view diagram illustrating an exploded view of a fluid flow resistor assembly and corresponding components according to embodiments herein.

FIG. 4 is an example perspective view diagram illustrating an exploded view of a fluid flow resistor assembly according to embodiments herein. In this example embodiment, the fluid flow resistor assembly 145-2 includes retainer 455, flow control assembly element 435, seal 425 (such as an elastomeric seal), port 310-1, and port 310-2. During operation, fluid pumped by fluid pump 110 is outputted from port 310-1 through opening 493-1 of seal 425 as indicated by fluid flow 478-1. The fluid further passes between a respective channel between facing 490-1 of the flow control assembly element 435 and the seal 425 to opening 493-2 in seal 425. As further indicated by fluid flow 478-2, the fluid passes through opening 493-2 of seal 425 into port 310-2 disposed on facing 492 of cassette 105.

Figure 5:
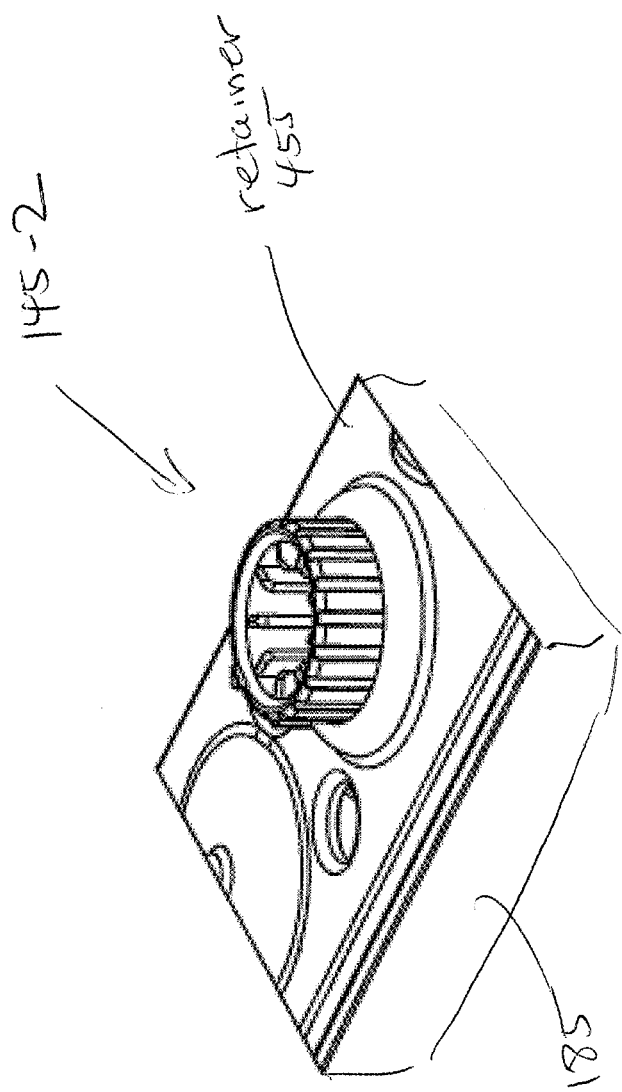
FIG. 5 is an example perspective view diagram illustrating a fluid flow resistor assembly according to embodiments herein.

FIG. 5 is an example perspective view diagram illustrating a fluid flow resistor assembly according to embodiments herein.

In this example embodiment, the retainer 455 applies a respective force to flow control assembly element 435, sandwiching the seal 425 between facing 490-1 of flow control assembly element 435 and facing 490-2 of cassette 185.

Figure 6:
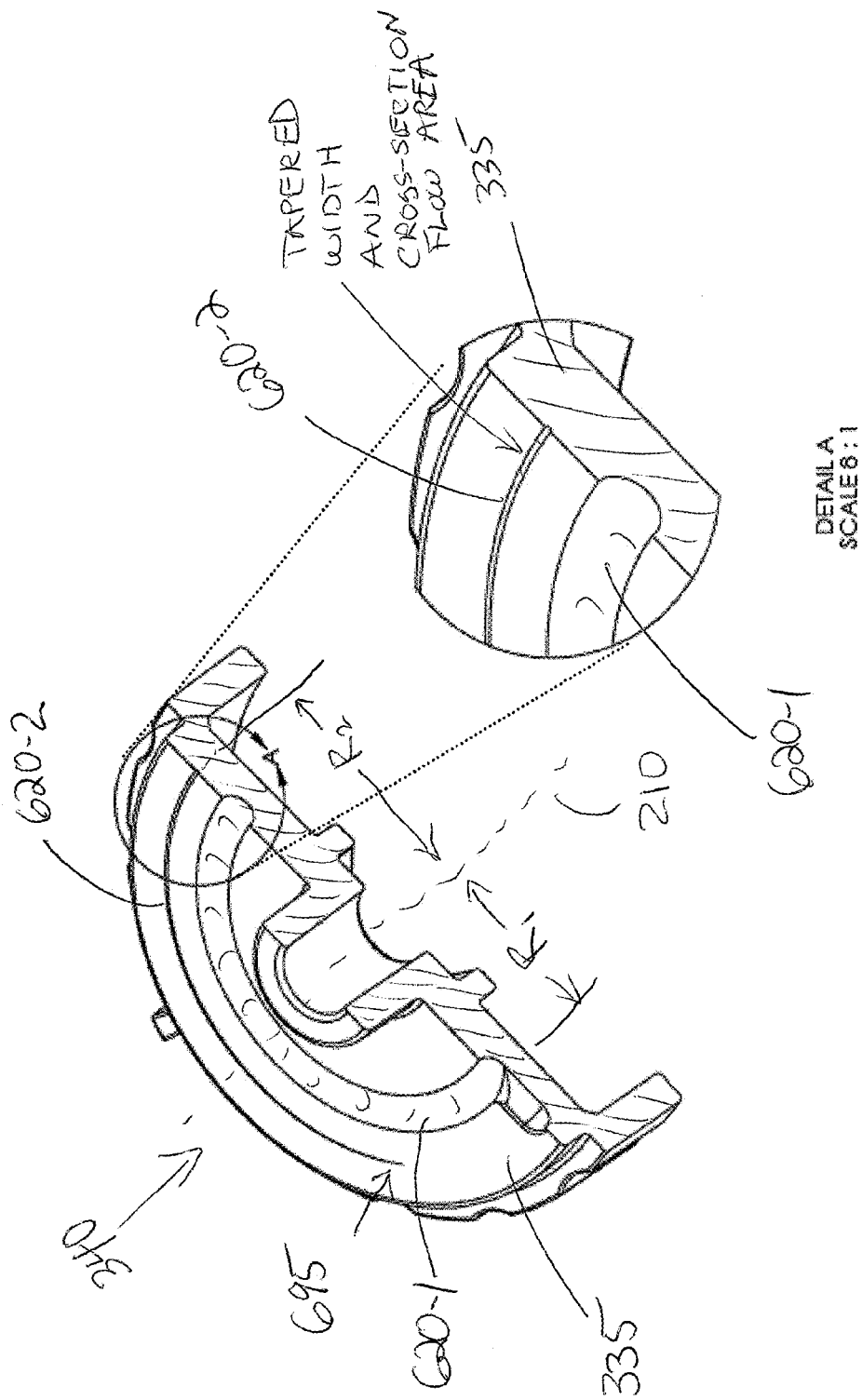
FIG. 6 is an example perspective view diagram illustrating a fluid pathway disposed on respective facing of a flow control assembly element according to embodiments herein.

FIG. 6 is an example perspective view diagram illustrating a fluid pathway disposed on respective facing of a flow control assembly element according to embodiments herein.

As shown, facing 340 of the fluid control assembly element 335 includes fluid pathway 620-1 and fluid pathway 620-2. Each fluid pathway is disposed at a different radius with respect to axis 210 through the center of flow control assembly element 335. For example, fluid pathway 620-1 is configured to reside on facing 340 at a first radius, R1, with respect to axis 210; fluid pathway 620-2 is configured to reside on facing 340 at a second radius, R2, with respect to axis 210.

As further shown, the width and cross-section (orthogonal to the flow fluid) of first fluid pathway 620-1 is substantially constant. In contrast, the width and cross-section (orthogonal to the flow of fluid) of the fluid pathway 620-2 tapers along a respective length of fluid pathway 620-2 to termination 695.

Figure 7:
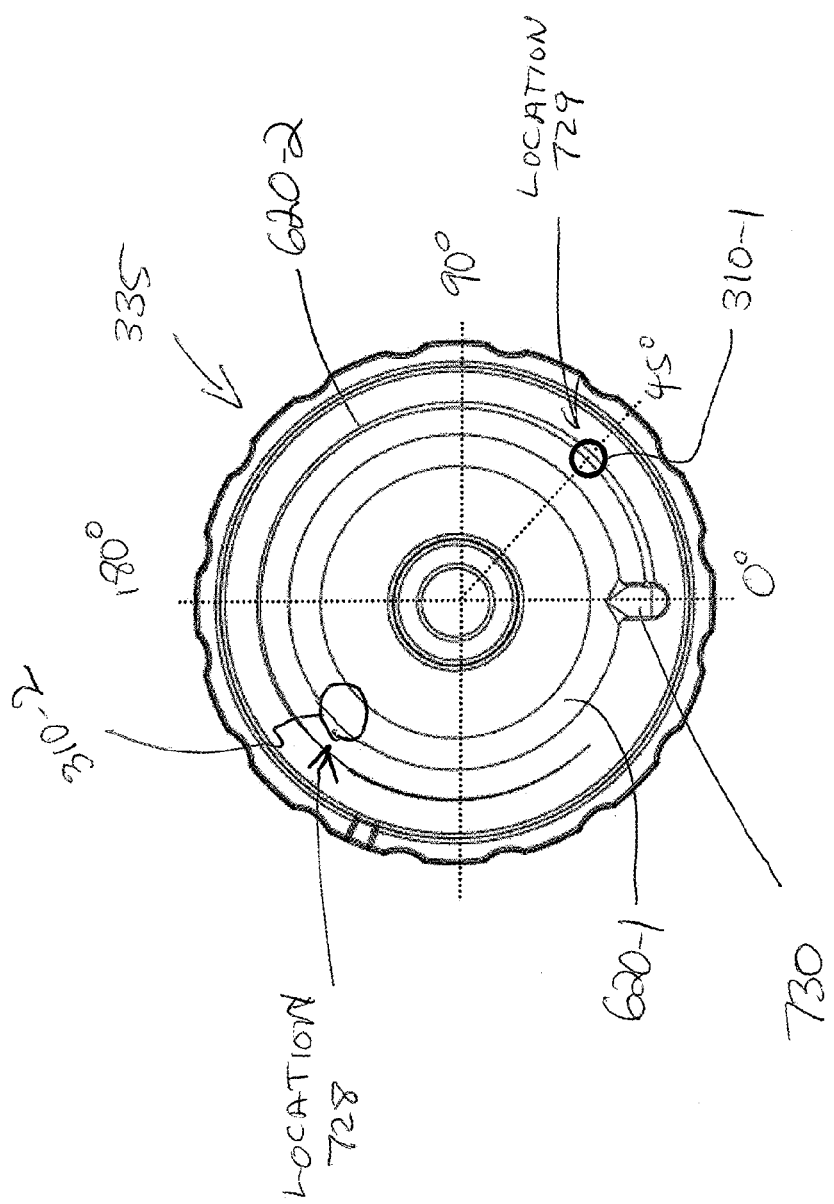
FIG. 7 is an example diagram illustrating an orientation of multiple ports with respect to a facing of a flow control assembly element according to embodiments herein.

FIG. 7 is an example diagram illustrating an orientation of multiple ports with respect to a facing of a respective flow control assembly element according to embodiments herein.

Assume in this example embodiment that the ports 310-1 (327-1) and 320-2 (327-2) are disposed (on cassette 185) opposite each other with respect to the center of fluid control assembly element 335. As shown, and as previously discussed, the fluid flow control assembly 335 rotates about axis 210 (recall that axis 210 extends orthogonally into and out of the respective page).

As shown in FIG. 7, port 310-1 is disposed at an angle of 45° over fluid pathway 620-2; port 310-2 (327-2) is disposed at angle 225° over fluid pathway 620-1.

During operation, in one non-limiting example embodiment, fluid flows through port 310-1 (327-1) into fluid pathway 620-2 at location 729, along fluid pathway 620-2 from location 729 to fluid channel 730, through fluid channel into fluid pathway 620-1. The fluid further flows counter-clockwise and/or clockwise along fluid pathway 620-1 from channel 730 to port 310-2 (327-2) at location 728. In general, because channel 730 and corresponding fluid pathway 620-1 are wide and relatively deep compared to dimensions of fluid pathway 620-2, fluid pathway 620-1 imparts relatively little fluid resistance to a flow of fluid between the overall fluid pathway from port 310-1 to port 310-2.

Figure 8:
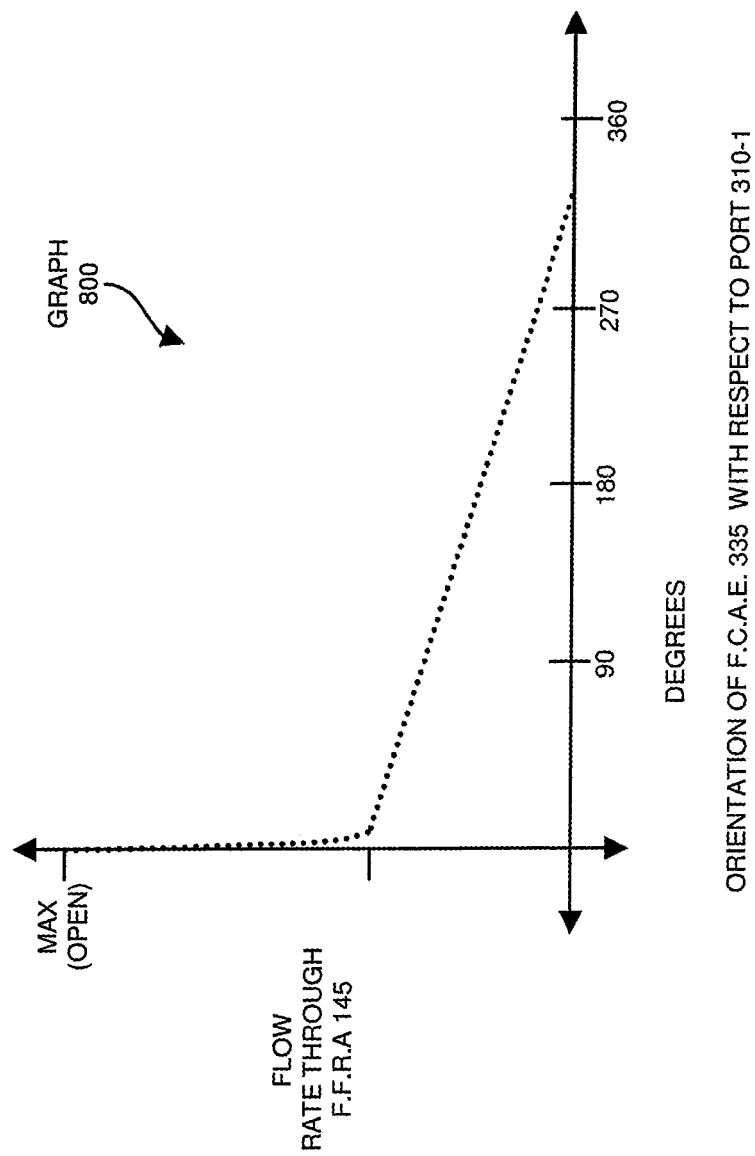
FIG. 8 is an example diagram illustrating a graph of fluid flow rate versus rotational setting of a fluid flow resistor assembly according to embodiments herein.

FIG. 8 is an example diagram illustrating a graph of fluid flow rate versus rotational setting of a fluid flow resistor assembly according to embodiments herein.

As previously discussed, an angular orientation of the respective flow control assembly element 335 controls a flow rate of fluid passing through the fluid flow resistor assembly 145. Graph 800 illustrates that fluid flow resistor assembly 145 provides increased flow resistance of fluid as the respective flow control assembly element 335 is increased from 0° to approximately 315°. Between 350° and approximately 357°, the fluid flow resistor assembly 145 blocks a respective flow of fluid from the port 310-1 (327-1) to the port 310-2 (327-2).

When the port 310-1 (327-1) is positioned over passageway 730, the fluid flow resistor 145 is set to a full open position (least resistance position). Rotating the respective fluid control assembly element 335 to 4° or greater angular value increases fluid resistance, causing the respective flow fluid rate through a fluid pathway 620 to linearly decrease to zero at approximately 315° at which point port 310-1 (327-1) is completely blocked between 315° and 357°.

In accordance with further embodiments, note that the profile of any or all of the fluid pathway 620 (fluid pathway 620-1, fluid pathway 620-2, etc.) can be adjusted to change the shape of the adjustment response curve in the graph 800 shown in FIG. 8. For example, the graph 800 can be linear (as shown), as well as logarithmic or some other desired profile simply based on modifications to parameters such as the width and depth of the fluid pathway along its length.

Figure 9:
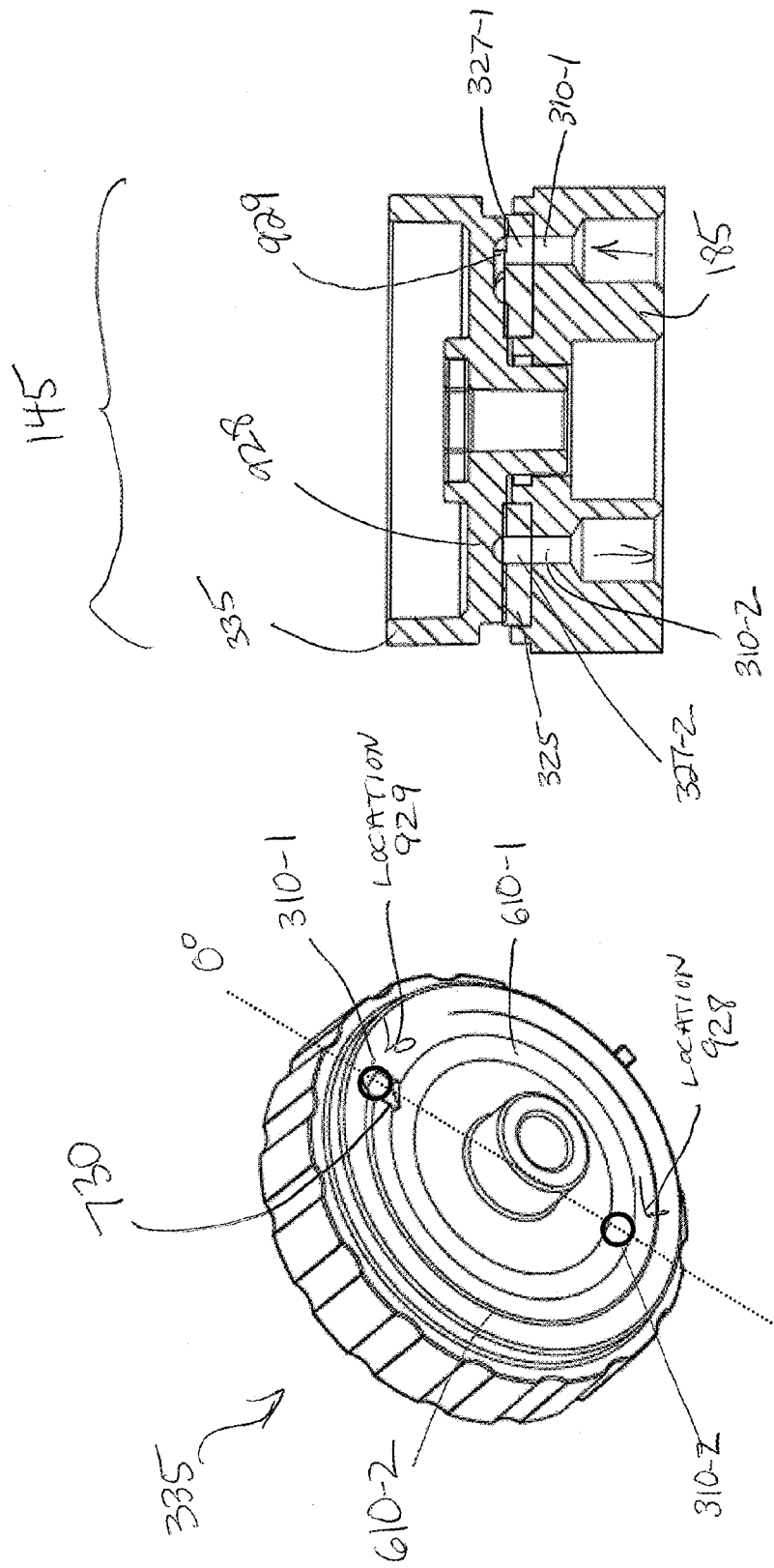
FIG. 9A is an example perspective view diagram of a fluid flow resistor assembly according to embodiments herein.
FIG. 9B is an example side view cutaway diagram of a fluid flow resistor assembly according to embodiments herein.

FIG. 9A is an example perspective view diagram of a fluid flow resistor assembly according to embodiments herein.

As shown in this example embodiment, the flow control assembly element 335 (which is in contact with a facing of the seal 325) is rotated about axis 210 such that the port 310-1 (327-1) resides over fluid pathway 610-2 at location 929; port 310-2 (327-2) resides over fluid pathway 610-1 at location 928. This corresponds to a setting of 0°, which is a full open position (least fluid flow resistance) as shown in graph 800.

FIG. 9B illustrates a corresponding cutaway side view of the fluid flow resistance assembly 145 based on the 0° setting of the flow control assembly element 335 as discussed in FIG. 9A.

Figure 10:
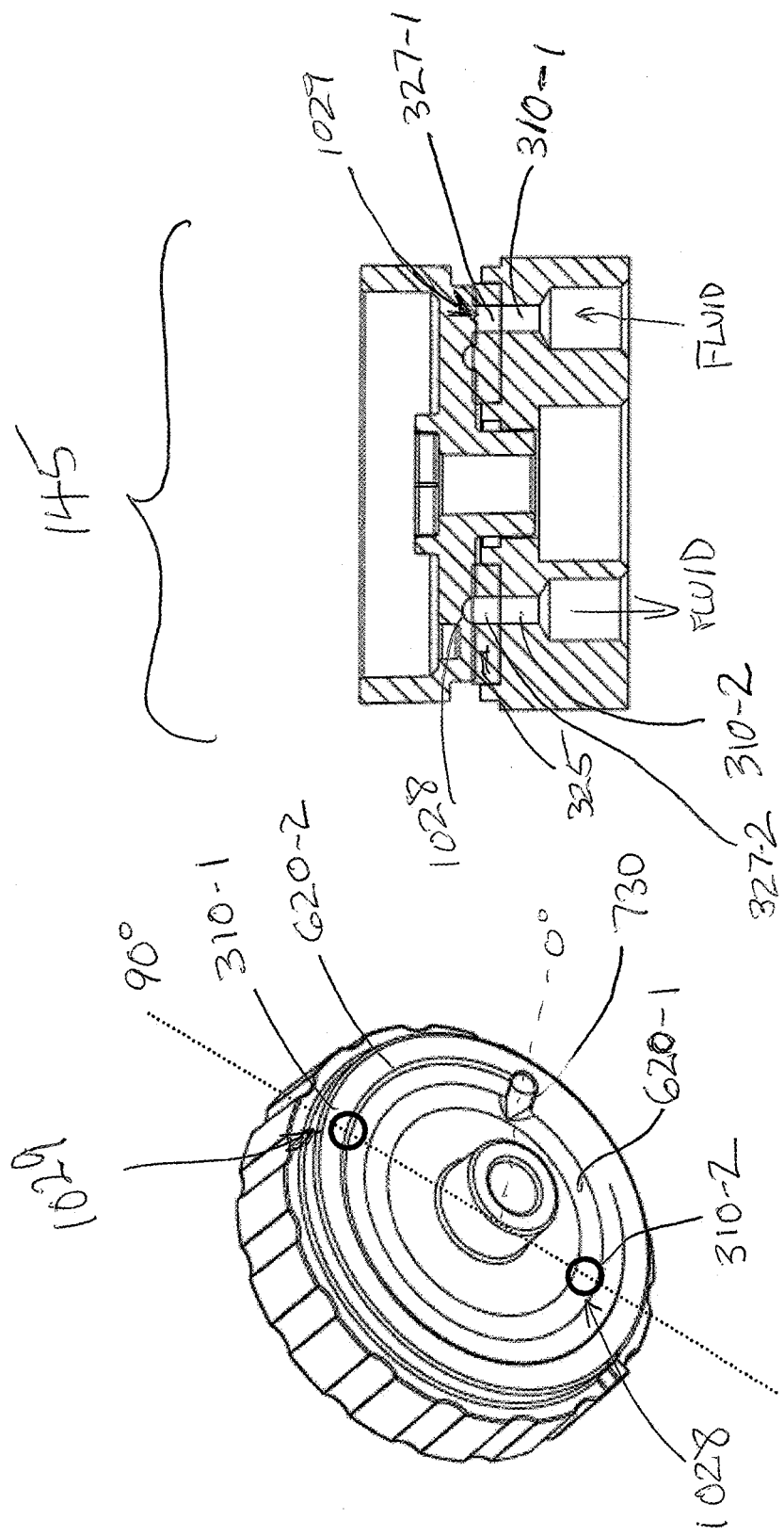
FIG. 10A is an example perspective view diagram of a fluid flow resistor assembly according to embodiments herein.
FIG. 10B is an example side view cutaway diagram of a fluid flow resistor assembly according to embodiments herein.

FIG. 10A is an example perspective view diagram of a fluid flow resistor assembly according to embodiments herein.

As shown in this example embodiment, the flow control assembly element 335 (which is in contact with a facing of the seal 325) is rotated about axis 210 such that the port 310-1 (327-1) resides over fluid pathway 610-2 at location 1029; port 310-2 (327-2) resides over fluid pathway 610-1 at location 1028. This corresponds to a setting of 90° as shown in graph 800. The width and depth of the fluid pathway 620-2 at location 1029 is substantially smaller than the width and depth of channel 730, resulting in a substantial decrease in fluid flow rate through a fluid pathway 620-2 between location 1029 and channel 730.

FIG. 10B illustrates a corresponding cutaway side view of the fluid flow resistance assembly 145 based on the setting (angular orientation of port 310-1 (327-1) at) 90°) of the flow control assembly element 335 as discussed in FIG. 10A.

Figure 11:
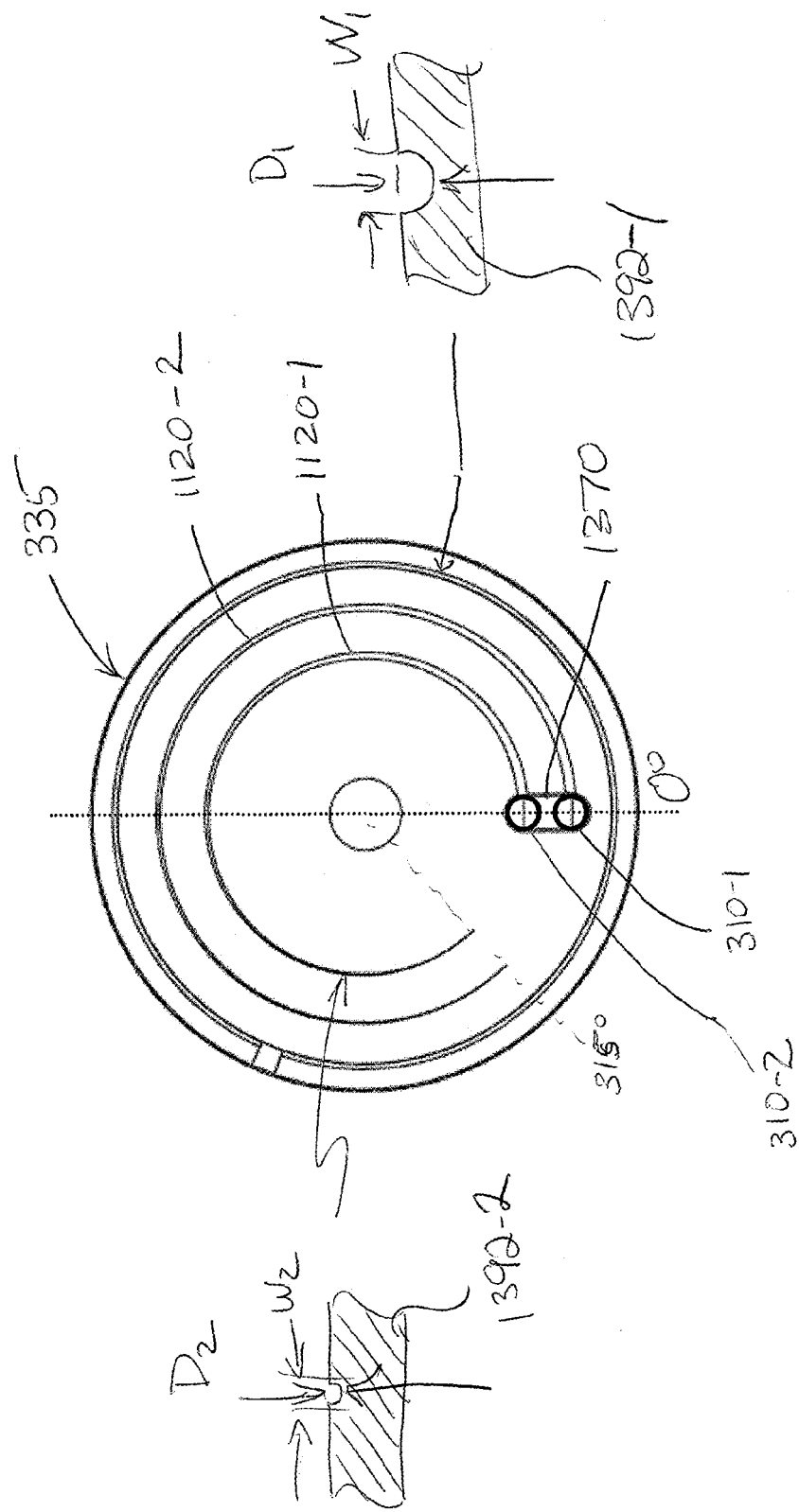
FIG. 11 is an example diagram illustrating orientation of a facing of a respective flow control assembly element in a first position according to embodiments herein.

FIG. 11 is an example diagram illustrating a facing of a respective flow control assembly element according to embodiments herein.

In this example embodiment, the flow control assembly element 335 includes multiple tapered fluid pathways. More specifically, flow control assembly element 335 includes inner fluid pathway 1120-1 and outer fluid pathway 1120-2. Similar to prior embodiments, an orientation of the ports 310-1 (327-1) and 310-2 (327-2) with respect to the fluid pathways 1120 dictates an amount of fluid flow resistance.

As further shown in FIG. 11, the fluid ports 310 are disposed at different radii with respect to a center of the flow control assembly element 335. In the selected position as shown, such as at 0° angular rotation, both port 310-1 (327-1) and port 310-2 (327-2) reside over channel 370 (a full open position). As shown in cross-sectional view 1392-2, the width W2 is substantially smaller than the width W1; is shown in cross-sectional view 1392-1, depth D2 is substantially smaller than depth D1. The cross-sectional area defined by depth D2 and width W2 provides substantially greater flow resistance than the cross-sectional area defined by depth D1 and width W1. Accordingly, rotation of the ports 310 (327) between 0° and 315° increases a respective fluid flow resistance provided by flow control assembly 335.

In accordance with further embodiments, note that width dimensions W1 and W2 can be the substantially same values along a length of fluid pathways 1120-1 and 1120-2 if desired. Additionally, depth dimensions D1 and D2 can be substantially the same along the length of fluid pathways 1120-1 and 1120-2. In such an instance, during a flow operation fluid passes through such fluid pathways 1120, this spreads out the pressure drop across more of the flow channels (fluid pathways 1120-1 and 1120-2). This embodiment provides a more gradual pressure drop along a length of the fluid pathway and can be advantageous for fluids or drugs that are very sensitive to turbulence and/or shear conditions.

Figure 12:
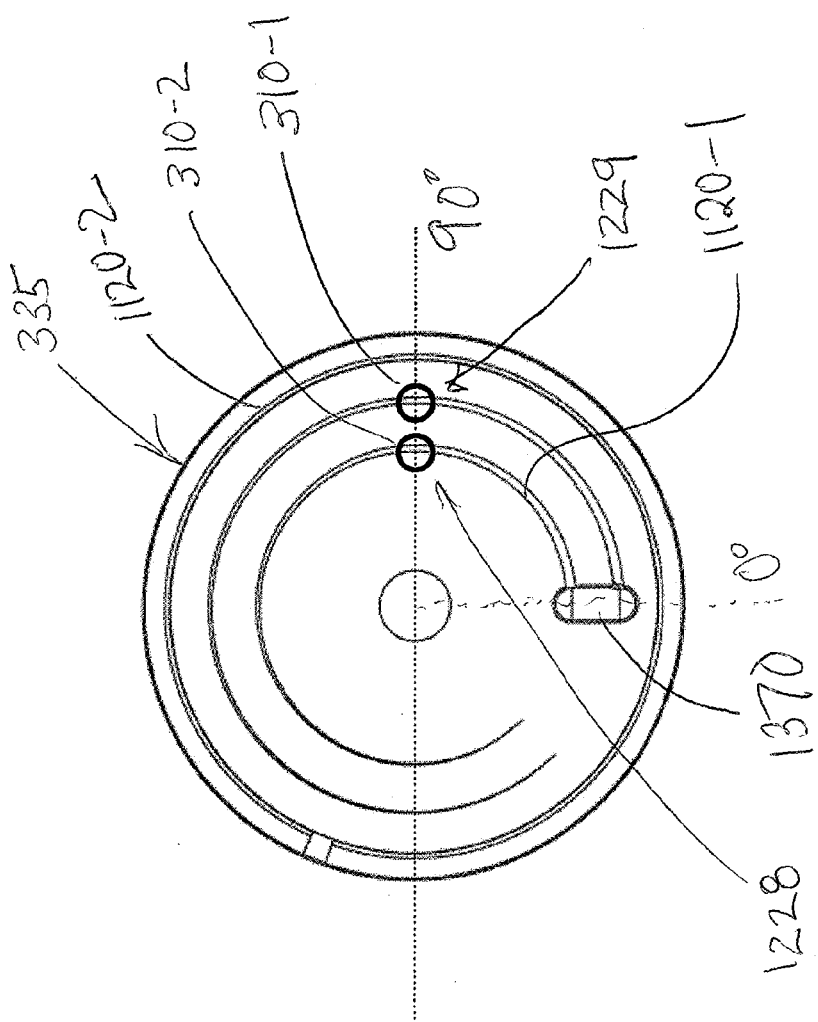
FIG. 12 is an example diagram illustrating orientation of a facing of the respective flow control assembly element and a second position according to embodiments herein.

FIG. 12 is an example diagram illustrating a facing of the respective flow control assembly element according to embodiments herein.

As further shown in FIG. 12, the fluid ports 310 (327) are disposed at a setting of 90° with respect to the full open position at 0°. In such an instance, at the 90° position, the port 310-2 (327-2) resides over inner fluid pathway 1120-1 at location 1228; port 310-1 (327-1) resides over outer fluid pathway 1120-2 at location 1229.

At the flow control settings of 90° as shown in FIG. 12, fluid flows: i) from port 310-1 (327-1) flows through outer fluid pathway 1120-2 at location 1229 to channel 1370; ii) through channel 1370 to inner fluid pathway 1120-1; iii) from channel 1370 along fluid pathway to port 310-2 (327-2) at location 1228.

Increasing the angular orientation of the flow control assembly element 335 to a higher angle than 90° causes the fluid flow resistance to increase.

Due to the aperture of the width of the fluid pathway 1120-1 at location 1228 into port 310-2 (327-2) and the aperture of the width of the fluid pathway 1120-2 at location 1229 into port 310-1 (327-1), as well as flow restriction provided by fluid pathways 1120-1 and 1120-2, the flow of fluid is substantially more restricted at the 90° setting of the fluid control assembly element 335 compared to flow resistance at 0° as previously discussed in FIG. 11.

Figure 13:
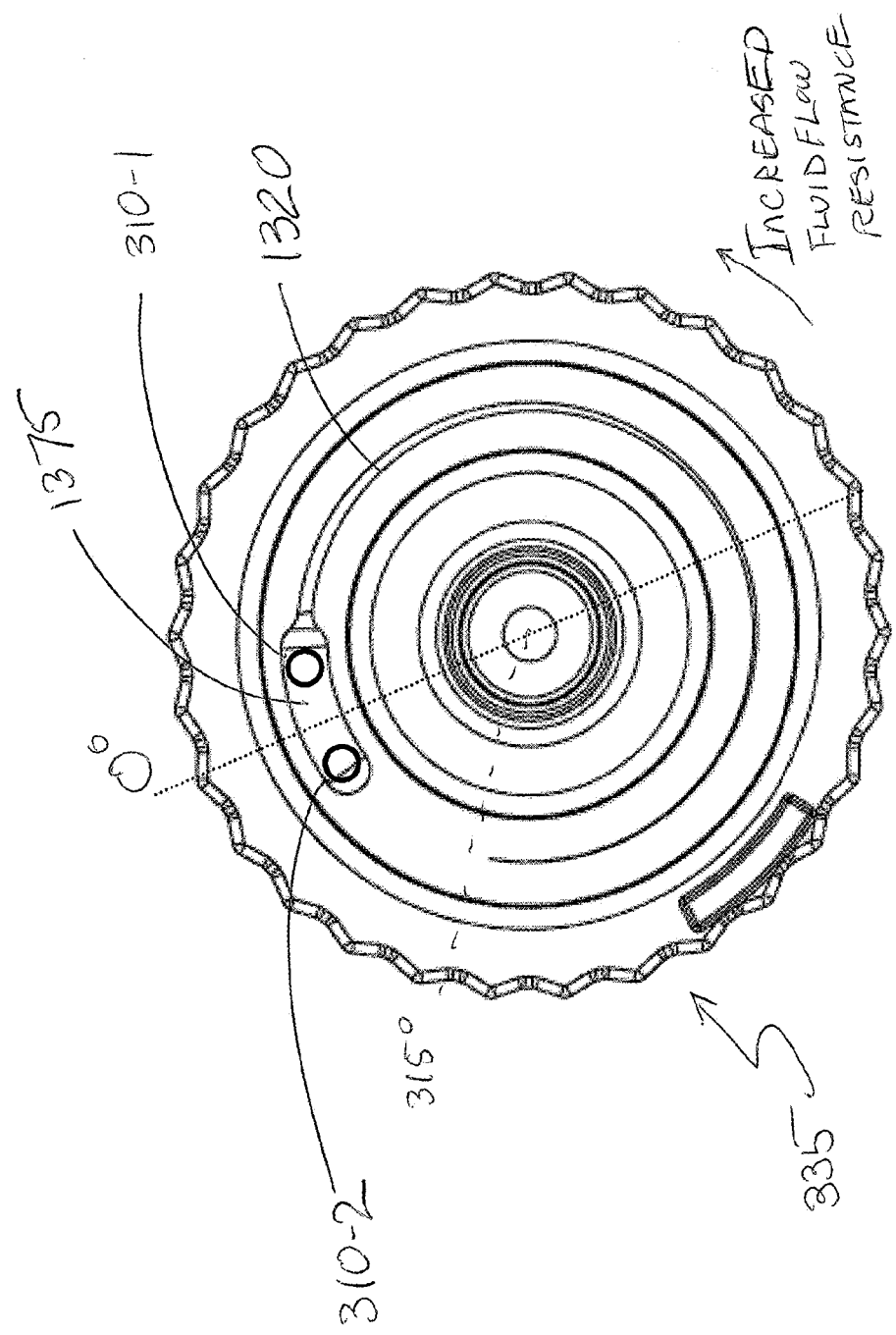
FIG. 13 is an example diagram illustrating orientation of a facing of a respective fluid flow control assembly element at a first position according to embodiments herein.

FIG. 13 is an example diagram illustrating a facing of a respective fluid flow control assembly element according to embodiments herein.

In this example embodiment, the flow control assembly element 335 includes a single fluid pathway 1320 disposed at a fixed radius with respect to center of flow control assembly element 335. As shown, the fluid pathway 1320 tapers between the 0° and 315° position. Further in this example embodiment, the corresponding ports 310-1 (327-1) and 310-2 (327-2) are disposed at the fixed radius with respect to the center of the flow control assembly element 335.

Similar to prior embodiments, an orientation of the ports 310-1 (327-1) and 310-2 (327-2) with respect to the fluid pathway 1320 dictates an amount of fluid flow resistance. Port 310-1 (327-1) and port 310-2 (327-2) are disposed at a fixed offset length with respect to each other on cassette 185.

While at the 0° position as shown, both port 310-1 (327-1) and port 310-2 (327-2) reside over a different location of fluid channel 1375. Fluid channel 1375 is a substantially large groove disposed in the flow control assembly element 335. Hence, when both port 310-1 (327-1) and port 310-2 (327-2) are disposed over fluid channel 1375, this corresponds to a full open position providing least fluid flow resistance. To provide increased fluid flow resistance, the flow control assembly element 335 is rotated counterclockwise with respect to ports 310-1 (327-1) and 310-2 (327-2).

Figure 14:
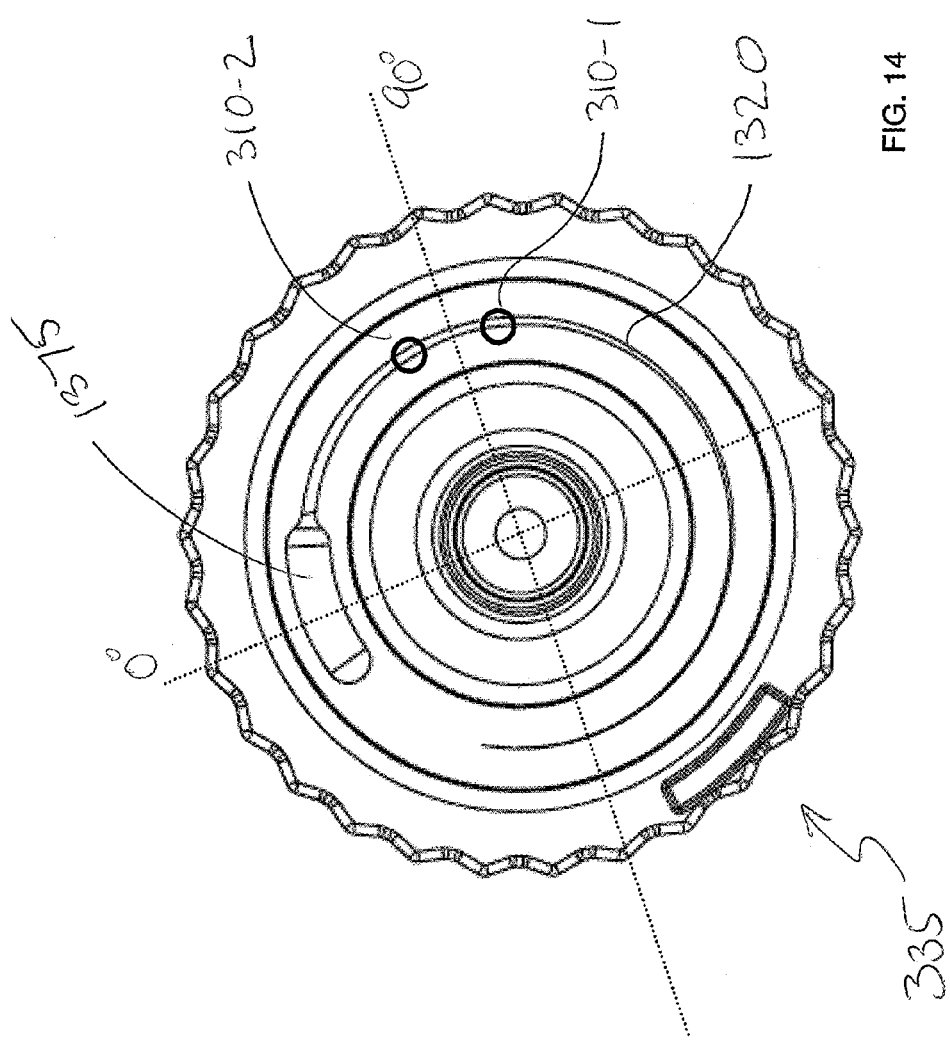
FIG. 14 is an example diagram illustrating orientation of a facing of a respective fluid flow control assembly element and a second position according to embodiments herein.

FIG. 14 is an example diagram illustrating a facing of a respective fluid flow control assembly element according to embodiments herein.

As mentioned, to provide increased fluid flow resistance, the flow control assembly element 335 is rotated counterclockwise with respect to ports 310-1 (327-1) and 310-2 (327-2) to 90°. While at the 90° position as shown, both port 310-1 (327-1) and 310-2 (327-2) reside over a respective narrowed portion of the fluid pathway 1320 as shown. To provide additional fluid flow resistance, the flow control assembly element 335 is rotated further counterclockwise with respect to ports 310-1 (327-1) and 310-2 (327-2).

Figure 15:
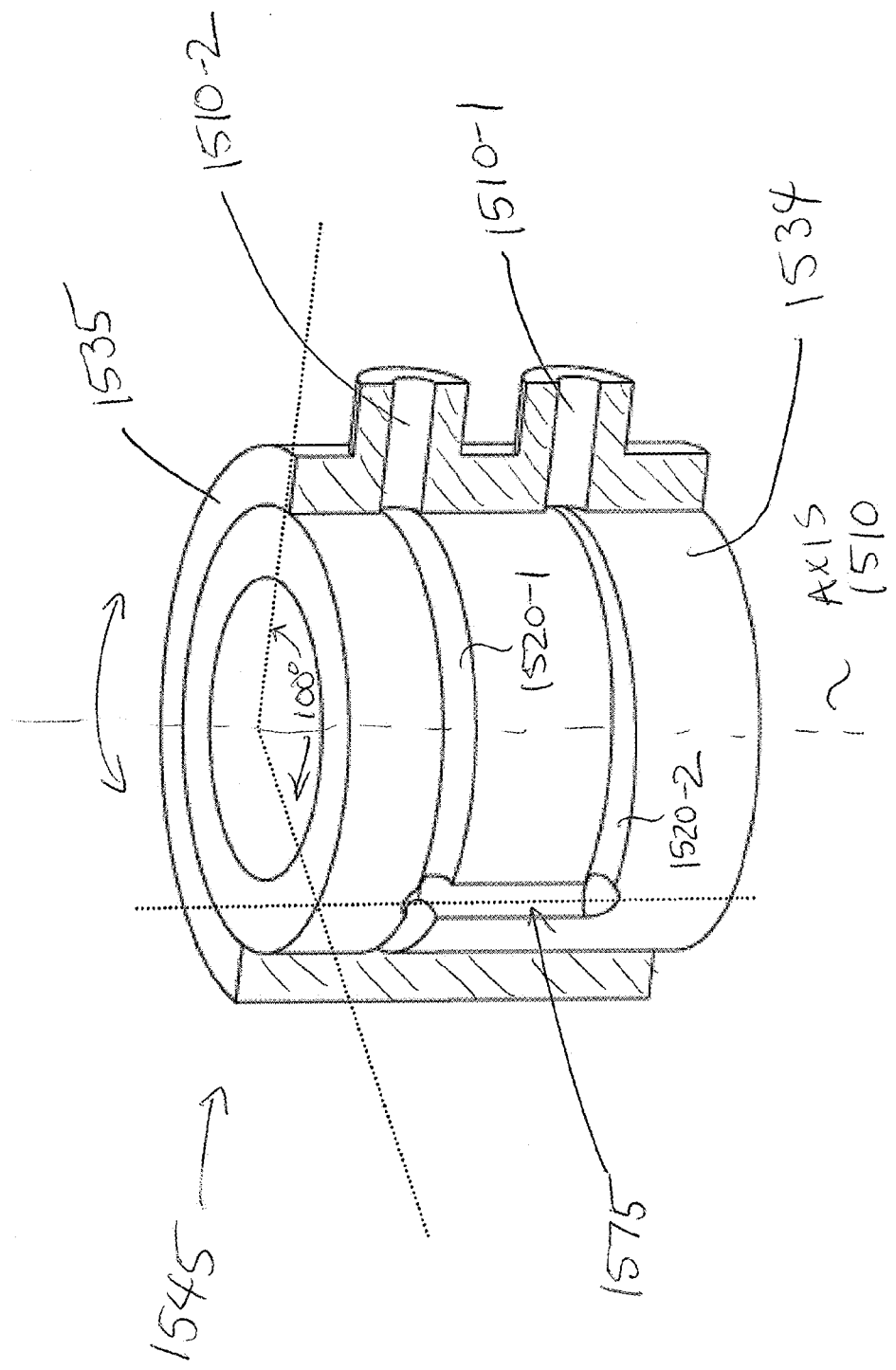
FIG. 15 is an example perspective cutaway view diagram of a fluid flow control assembly according to embodiments herein.

FIG. 15 is an example perspective cutaway view diagram of a fluid flow control assembly according to embodiments herein.

As shown, flow control assembly 1545 includes flow control assembly element 1535 and flow control assembly element 1534. A portion of fluid flow control assembly element 1535 is removed to show internal attributes of flow control assembly element 1534. The remote portion of flow control assembly element 1535 is symmetrical to the portion of flow control assembly element 1535 shown.

This example embodiment illustrates that the tapered fluid pathways need not be disposed on a respective planar surface of fluid flow assembly element 335 previous and discuss. For example, in this alternative example embodiment, flow control assembly element 1535 rotates as shown with respect to flow control assembly element 1534. Flow control assembly element 1504 includes fluid pathway 1520-1 and fluid pathway 1520-2 disposed as a hollowed volume on a cylindrical outer facing of a flow control assembly element 1534.

As shown, a width and/or depth of the hollowed volume (fluid pathway 1520) on the cylindrical facing varies along its length round the outer circumferential surface of flow control assembly element 1534.

As further shown, fluid channel 1575 connects fluid pathway 1520-1 and 1520-2 at a 0° setting, at which ports 1510-1 and port 1510-2 could potentially reside over fluid channel 1575 if moved to the 0° position (full open position). However, in this example embodiment, the flow control assembly element 1535 and corresponding ports 1510-1 and 1510-2 are disposed at a position 100° counterclockwise (as looking down axis 1510) with respect to fluid channel 1575 with respect to position 0°.

Flow restriction in this example embodiment is defined by resistance of fluid through a combination of port 1510-1, along fluid pathway 1520-2 between port 1510-1 and fluid channel 1575, through fluid channel 1575, along fluid pathway 1520-1 between fluid channel 1575 and port 1510-2.

To provide increased flow resistance, the flow control assembly element 1535 is rotated further counterclockwise (greater than 100°) with respect to channel 1575 of the flow control assembly element 1534.

Alternatively, note that if the flow control assembly element 1534 is the movable component in the flow control apparatus 1545, then the flow control assembly element 1534 is rotated further clockwise to greater than 100° with respect to flow control assembly element 1535 to increase fluid flow resistance. Conversely, the flow control assembly element 1534 can be rotated further counterclockwise to less than 100° to decrease fluid flow resistance.

In general, the narrowing of fluid pathway 1520-2 based on movement of the flow control assembly element 1534 and corresponding ports 1510 clockwise (to an angle greater than 100°) causes the fluid flow resistance to increase as the port 1510-1 is moved over a more narrow width and depth of the fluid pathway 1520-2.

Further, in a manner as previously discussed, note again that the fluid resistor drive 195 can be configured to control rotational orientation of the flow control assembly element 1534 with respect to the flow control assembly element 1535 to control a respective flow of fluid through cassette 185 to recipient 108. Note additionally that alternative embodiments of channels (fluid pathways 610) disposed on a rotatable planar surface as previously discussed in FIGS. 11-14 can be applied to the cylindrical surface configuration as discussed in FIG. 15.

Figure 16:
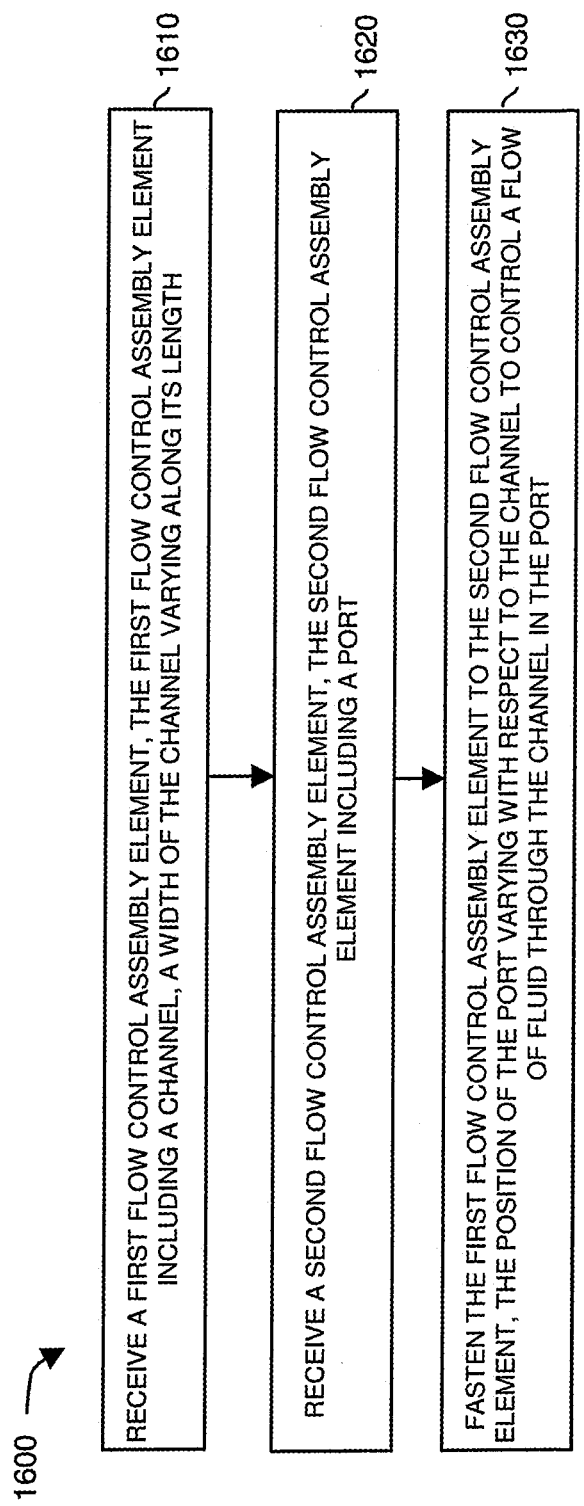
FIG. 16 is an example diagram illustrating a method of fabricating a flow control assembly according to embodiments herein.

FIG. 16 is an example diagram illustrating a method (as indicated by flow chart 1600) of fabricating a flow control assembly according to embodiments herein.

In processing block 1610, the fabrication resource (an assembler such as a machine, human, etc.) receives a first flow control assembly element 335. The first flow control assembly element 335 includes a channel (fluid pathway 620-2). The width of the fluid pathway 620-2 (channel) varies along its length.

In processing block 1620, the fabrication resource receives a second flow control assembly element (such as seal and 325 and/or cassette 185), the second flow control assembly element includes one or more ports 310.

In processing block 1530, the fabrication resource fastens the first flow control assembly element 335 to the second flow control assembly element, the position of the one or more ports 310 varies with respect to the channel to control a flow of fluid through the channel in the port. In one embodiment, the fastening of the first flow control assembly element 335 to the second flow control assembly element includes aligning the fluid pathway 620-2 to be slidable with respect to and in fluid communication with the port 310-1.

Figure 17:
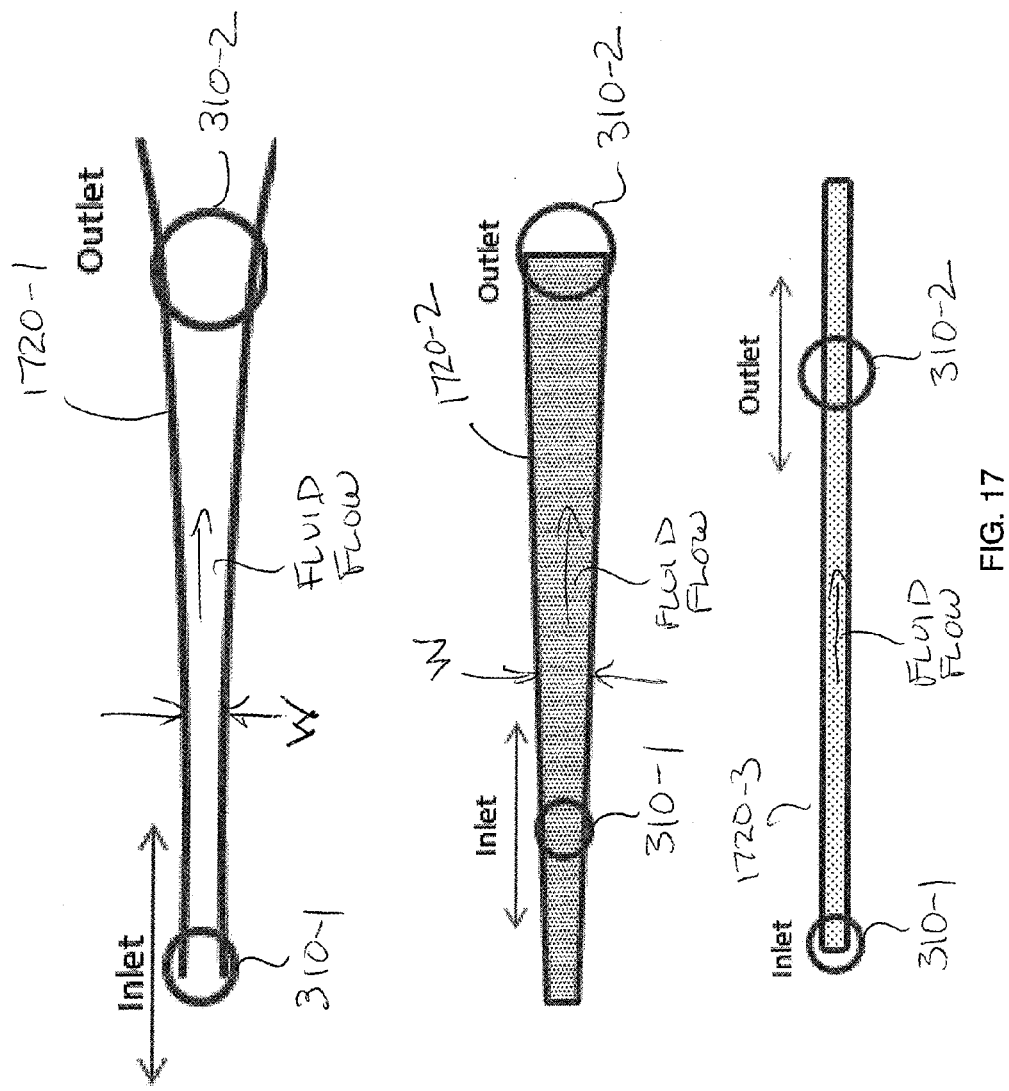
FIG. 17 is an example diagram illustrating multiple different ways of producing a fluid pathway and providing fluid flow resistance according to embodiments herein.

FIG. 17 is an example diagram illustrating multiple different ways of producing a fluid pathway and providing fluid flow resistance according to embodiments herein.

As shown, a width of the fluid pathway 1720-1 varies along its length. In this example embodiment, the width (W, as measured orthogonal to a fluid flow) varies at a nonlinear rate along the length. Port 310-1 (327-1) is movable along the length of the fluid pathway 1720-1. Movement of the port 310-1 (327-1) along fluid pathway 1720-1 closer to the port 310-2 (327-2) reduces a respective fluid flow resistance. Conversely, movement of the port 310-1 (327-1) further away from the port 310-2 (327-2) increases fluid flow resistance.

As shown, a width of the fluid pathway 1720-2 varies along its length. In this example embodiment, the width (W, as measured orthogonal to a fluid flow) varies at a linear rate along the length. Port 310-1 (327-1) is movable along the length of the fluid pathway 1720-2. Movement of the port 310-1 (327-1) along fluid pathway 1720-2 closer to the port 310-2 (327-2) reduces a respective fluid flow resistance. Conversely, movement of the port 310-1 (327-1) further away from the port 310-2 (327-2) on fluid pathway 1720-2 increases fluid flow resistance.

As shown, a width of the fluid pathway 1720-3 is substantially constant along its length. Port 310-1 (327-1) is movable along the length of the fluid pathway 1720-3. Movement of the port 310-1 (327-1) along fluid pathway 1720-3 closer to the port 310-2 (327-2) reduces a respective fluid flow resistance. Conversely, movement of the port 310-1 (327-1) further away from the port 310-2 (327-2) on fluid pathway 1720-2 increases fluid flow resistance.

As previously discussed, in further embodiments, note that both the inlet (such as port 310-1) and outlet (such as port 310-2) can be configured to move along the respective fluid pathway at a fixed distance between each other.

Figure 18:
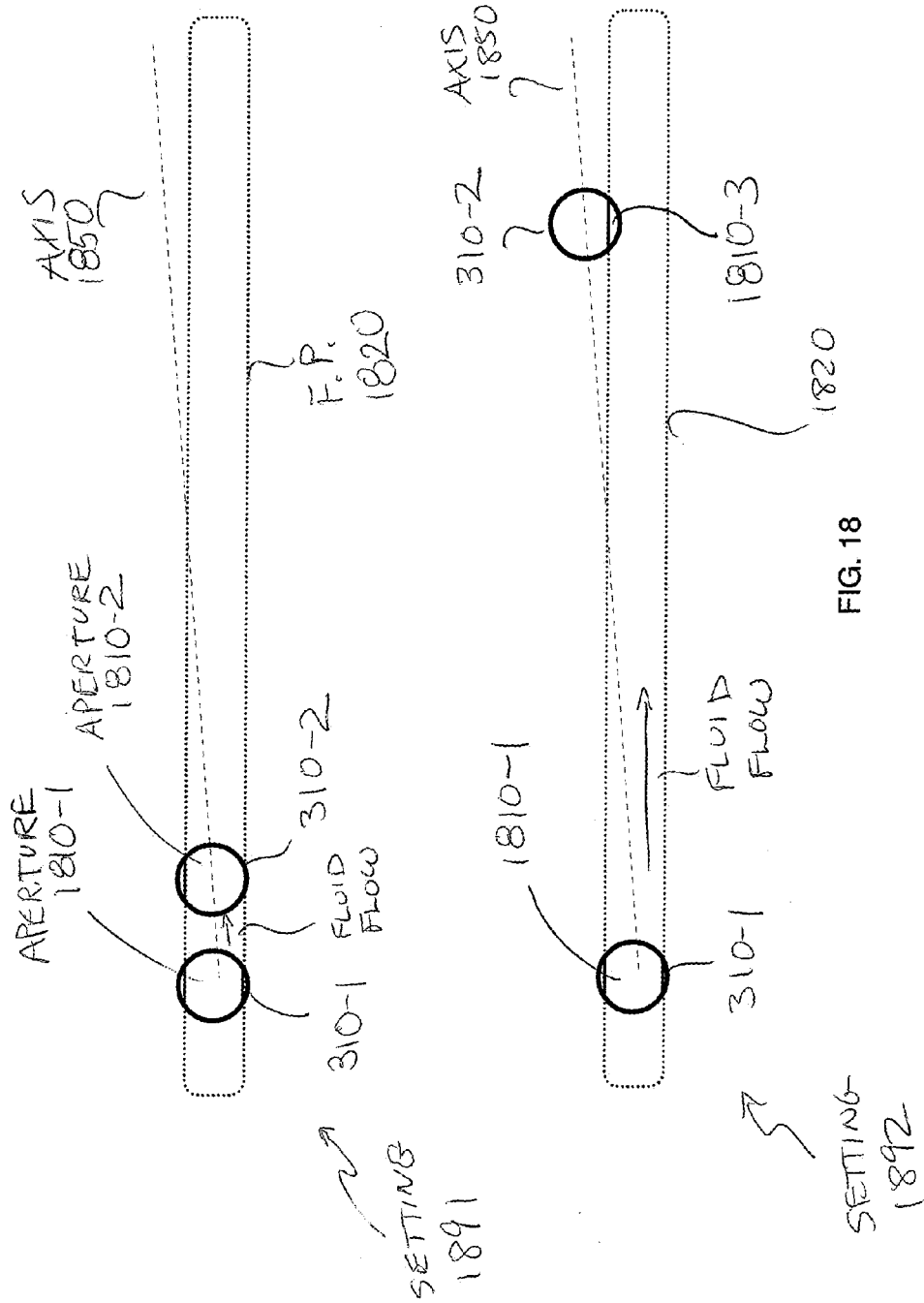
FIG. 18 is an example diagram illustrating a change in respective aperture of a port to control fluid flow according to embodiments herein.

FIG. 18 is an example diagram illustrating a change in respective aperture of a port to control fluid flow according to embodiments herein.

As shown, the fluid pathway 1820 is disposed in a respective substrate. Assume in this example embodiment that port 310-1 resides at a fixed location with respect to the fluid pathway 1820. A centroid of port 310-2 is restricted to movement along axis 1850.

With reference to the first setting 1891, port 310-1 has an aperture 1810-1 (window) into fluid pathway 1820. Port 310-2 has an aperture 1810-2. In a manner as previously discussed, fluid flows through aperture 1810-1 of port 310-1 through fluid pathway 1820 and out of aperture 1810-2 of port 310-2. Because the port 310-2 is relatively close to port 310-1, and because apertures 1810 are any full open position, the fluid resistance provided by setting 1891 is relatively low.

With reference to the second setting 1892, port 310-1 has an aperture 1810-1 (window) into fluid pathway 1820. Port 310-2 has an aperture 1810-3. In a manner as previously discussed, fluid flows through aperture 1810-1 of port 310-1 through fluid pathway 1820 and out of aperture 1810-2 of port 310-2. Because the port 310-2 is relatively far away from port 310-1, and because aperture 1810-3 is substantially smaller than aperture 1810-2, the fluid resistance provided by setting 1892 is substantially higher than the resistance provided by setting 1891.

Note again that techniques herein are well suited for use in any suitable type of fluid delivery system including a fluid flow restrictor. However, it should be noted that embodiments herein are not limited to use in such applications and that the techniques discussed herein are well suited for other applications as well.

Based on the description set forth herein, numerous specific details have been set forth to provide a thorough understanding of claimed subject matter. However, it will be understood by those skilled in the art that claimed subject matter may be practiced without these specific details. In other instances, methods, apparatuses, systems, etc., that would be known by one of ordinary skill have not been described in detail so as not to obscure claimed subject matter. Some portions of the detailed description have been presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm as described herein, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has been convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing platform, such as a computer or a similar electronic computing device, that manipulates or transforms data represented as physical electronic or magnetic quantities within memories, registers, or other information storage devices, transmission devices, or display devices of the computing platform.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

We claim:

1. A flow control assembly comprising:
   a fluid pump to pump fluid;
   a fluid flow resistor assembly to resist a flow of the fluid, the fluid flow resistor assembly comprising a first assembly component and a second assembly component;
   the first assembly component including a length of fluid channel, the fluid channel formed in a surface facing of the first assembly component to convey the fluid;
   the second assembly component movable with respect to the first assembly component, a surface facing of the second assembly component in contact with the surface facing of the first assembly component and the fluid in the fluid channel to retain flow of the fluid to be within the fluid channel of the first assembly component, the second assembly component including a first port and a second port;
   an opening of the first port positioned with respect to the fluid channel at a first location along the length of the fluid channel;
   an opening of the second port positioned with respect to the fluid channel at a second location along the length;
   wherein the second assembly component is rotatable about an axis with respect to the first assembly component, a first angular position of the second assembly component with respect to the first assembly component about the axis resulting in a full open setting of both the opening of the first port and the opening of the second port into a first channel segment of the fluid channel, the first channel segment being continuous;
   wherein the opening of the first port resides at a fixed radius with respect to the axis; and
   wherein the opening of the second port resides at the fixed radius with respect to the axis;
   wherein the fluid channel includes a second channel segment, a width of the fluid channel in the second channel segment varying to provide variable fluid flow resistance.

2. The flow control assembly as in claim 1, wherein the fluid channel is movable with respect to the opening of the first port and the opening of the second port to adjust a fluid flow resistance through a combination of the first port, a portion of the fluid channel between the first location and the second location, and the second port.

3. The flow control assembly as in claim 2, wherein the opening of the first port is disposed to be at a fixed offset distance with respect to the opening of the second port.

4. The flow control assembly as in claim 1, wherein an aperture of the fluid channel into the opening of the first port at the first location and an aperture of the fluid channel into the opening of the second port at the second location controls an amount of fluid flow resistance of fluid passing along the fluid channel from the first port to the second port.

5. The flow control assembly as in claim 1, wherein a cross-sectional flow area of the fluid channel orthogonal to a flow of the fluid through the fluid channel varies along the length.

6. The flow control assembly as in claim 1, wherein a width of the fluid channel orthogonal to a flow of fluid through the fluid channel varies along the length.

7. The flow control assembly as in claim 1, wherein the surface facing of the first assembly component is planar;
   wherein the surface facing of the second assembly component is planar.

8. The flow control assembly as in claim 7, wherein the length of the fluid channel is curved.

9. The flow control assembly as in claim 1, wherein the surface of the first assembly component is a cylindrical facing.

10. The flow control assembly as in claim 1, wherein the first port resides at a fixed location of the fluid channel; and
    wherein the opening of the second port is movable along the length of the fluid channel with respect to the opening of the first port.

11. The flow control assembly as in claim 1, wherein the width of the fluid channel at the first location defines a first aperture through which fluid flows through the opening of the first port into the fluid channel at the first location.

12. The flow control assembly as in claim 11, wherein the width of the fluid channel at the second location defines a second aperture through which fluid from the fluid channel at the second location flows from the fluid channel through the opening of the second port into the second port.

13. The flow control assembly as in claim 12, wherein the first aperture, the second aperture, and flow resistance provided by the fluid channel regulate a flow of the fluid to a respective target recipient.

14. The flow control assembly as in claim 1, wherein a portion of the surface facing of the second assembly component in contact with the fluid in the fluid channel extends continuously between the opening of the first port and the opening of the second port to retain the flow of fluid to be in the fluid channel between the opening of the first port and the opening of the second port.

15. The flow control assembly as in claim 1, wherein the surface facing of the second assembly component includes a first surface portion and a second surface portion, the first surface portion in contact with the fluid in the fluid channel and the second surface portion in contact with the surface facing of the first assembly component to retain the fluid in the fluid channel while the fluid is conveyed from the first port to the second port.

16. The flow control assembly as in claim 15, wherein the first surface portion and corresponding walls of the fluid channel in the first assembly component define a fluid pathway between the opening of the first port and the opening of the second port.

17. The flow control assembly as in claim 1, wherein the opening of the second port receives the fluid from the fluid channel in only a single direction of flow from the fluid channel.

18. The flow control assembly as in claim 1, wherein contacting the surface facing of the second assembly component to the surface facing of the first assembly component limits the flow of the fluid through the fluid channel in a downstream direction from the first port to the second port.

19. The flow control assembly as in claim 1, wherein the surface facing of the second assembly component in contact with the surface facing of the first assembly component limits the flow of the fluid through the fluid channel to a single direction.

20. The flow control assembly as in claim 1, wherein a cross-sectional flow area of the second channel segment orthogonal to a flow of the fluid through the second channel segment varies non-linearly along the length.

21. The flow control assembly as in claim 20, wherein the fluid flow resistor assembly provides linear resistance variation in flow resistance per degree of rotation of the second assembly component.

22. The flow control assembly as in claim 1 further comprising:
a cassette frame in which the fluid flow resistor assembly and the fluid pump are integrated, the flow control assembly insertable into a cavity of a fluid delivery system that controls the fluid pump and the fluid flow resistor assembly to provide flow regulation via a closed loop control algorithm.

23. The flow control assembly as in claim 1, wherein at least one angular position of the second assembly component with respect to the first assembly component about the axis results in complete blockage of both the opening of the first port and the opening of the second port.

24. The flow control assembly as in claim 1, wherein the fluid channel is disposed on a cylindrical surface of the second assembly component.

25. The flow control assembly as in claim 24, wherein the first channel portion is offset with respect to the second channel portion; and
wherein the second channel portion is parallel with respect to the first channel portion.

26. The flow control assembly as in claim 1, wherein a relationship between a change in angular rotation of the second flow control assembly element with respect to the first flow control assembly element and resulting change in the flow rate of fluid through the channel is linear.

27. The flow control assembly as in claim 1, wherein the second channel segment is a tapered channel segment providing increased flow resistance in a range of selectable angular positions in which both the first opening of the first port and the opening of the second port reside over the second channel segment.

28. A flow control apparatus comprising:
a first flow control assembly element including a channel operable to convey fluid, a width of the channel varying along a length of the channel; and
a second flow control assembly element in contact with the first flow control assembly element, the second flow control assembly element including a first port in fluid communication with the channel, a position of the first port of the second flow control assembly element adjustable with respect to the channel disposed on the first flow control assembly element to control a flow rate of the fluid through the channel;
wherein the second flow control assembly element includes a second port, the second port of the second flow control assembly in fluid communication with the channel disposed on the first flow control assembly element;
wherein a relationship between a change in angular rotation of the second flow control assembly element with respect to the first flow control assembly element and resulting change in the flow rate of fluid through the channel is linear;
wherein the second assembly component is rotatable about an axis with respect to the first assembly component, at least one angular position of the second assembly component with respect to the first assembly component about the axis resulting in complete blockage of both the opening of the first port and the opening of the second port; and
wherein the opening of the first port resides at a fixed radius with respect to the axis; and
wherein the opening of the second port resides at the fixed radius with respect to the axis.

29. The flow control apparatus as in claim 28, wherein the channel is disposed on a planar surface of the first flow control assembly element.

30. The flow control apparatus as in claim 29, wherein the second flow control assembly element is fabricated from rigid material; and
wherein the first port and the second port of the second flow control assembly element are disposed at respective fixed locations on the second flow control assembly element.

31. The flow control apparatus as in claim 30, wherein the second flow control assembly element includes a planar surface region through which the first port and the second port are in fluid communication with the channel disposed on the first flow control assembly element; and
wherein a surface region of the second flow control assembly element slidably covers the channel, the combination of the surface region and the channel creating a fluid-tight passageway between the first port and the second port, the fluid inputted from the first port to a first location of the channel, passing through the fluid-tight passageway, and outputted from a second location of the channel into the second port.

32. The flow control apparatus as in claim 28, wherein the channel is disposed in a substantially planar surface of the first flow control assembly element; and
wherein the first port is disposed through a substantially planar surface of the second flow control assembly element, the substantially planar surface of the second flow control assembly element in contact with the substantially planar surface of the first flow control assembly element.

33. The flow control apparatus as in claim 32, wherein the second flow control assembly element rotates with respect to the first flow control assembly element, variations in an angle of the rotation of the second flow control assembly element with respect to the first flow control assembly element controlling a flow rate of the fluid passing through the channel and the first port.

34. A flow control assembly comprising:
a fluid pump to pump fluid;
a fluid flow resistor assembly to resist a flow of the fluid, the fluid flow resistor assembly comprising a first assembly component and a second assembly component;
the first assembly component including a length of fluid channel, the fluid channel formed on a planar surface facing of the first assembly component to convey the fluid;
the second assembly component movable with respect to the first assembly component, a surface facing of the second assembly component in contact with the planar surface facing of the first assembly component and the fluid in the fluid channel to retain flow of the fluid to be within the fluid channel of the first assembly component, the second assembly component including a first port and a second port;

an opening of the first port positioned with respect to the fluid channel at a first location along the length of the fluid channel; and an opening of the second port positioned with respect to the fluid channel at a second location along the length, a width of the fluid channel at the first location into the opening of the first port different than a width of the fluid channel at the second location into the opening of the second port;

wherein the fluid channel includes a first channel portion and a second channel portion, the first channel portion disposed at a first radius from a rotational axis about which the second assembly component rotates, the second channel portion disposed at a second radius from the rotational axis.

35. The flow control assembly as in claim 34, wherein the opening of the first port resides arc still and is movable over the first channel portion at the first radius; and wherein the opening of the second channel portion resides and is movable over the second channel portion at the second radius.

36. The flow control assembly as in claim 35, wherein the fluid channel further includes a third channel portion connecting the first channel portion to the second channel portion, the third channel portion being orthogonal to the first channel portion of the second channel portion.

37. The flow control assembly as in claim 36, wherein the first channel portion is a continuous channel extending 360 degrees along the first radius; and wherein the second channel portion is a discontinuous channel along the second radius.

38. The flow control assembly as in claim 37, wherein a cross-sectional flow area of the continuous channel orthogonal to a flow of the fluid through the continuous channel is fixed; and wherein a cross-sectional flow area of the discontinuous channel orthogonal to the flow of the fluid through the discontinuous channel varies.

39. The flow control assembly as in claim 34, wherein a cross-sectional flow area of the first channel portion varies along a length of the first channel portion; and wherein a cross-sectional flow area of the second channel portion varies along a length of the second channel portion.

* * * * *